United States Patent
Zhadkevich

(10) Patent No.: US 9,913,967 B2
(45) Date of Patent: Mar. 13, 2018

(54) OCCLUDING CATHETER AND DYNAMIC METHOD FOR PREVENTION OF STROKE

(71) Applicant: Michael Zhadkevich, Inman, SC (US)

(72) Inventor: Michael Zhadkevich, Inman, SC (US)

(*) Notice: Subject to any disclaimer, the term of this patent is extended or adjusted under 35 U.S.C. 154(b) by 839 days.

(21) Appl. No.: 14/310,681

(22) Filed: Jun. 20, 2014

(65) Prior Publication Data
US 2014/0336690 A1    Nov. 13, 2014

Related U.S. Application Data

(63) Continuation-in-part of application No. 13/918,492, filed on Jun. 14, 2013, now Pat. No. 9,498,225.
(Continued)

(51) Int. Cl.
*A61M 29/00* (2006.01)
*A61M 25/10* (2013.01)
(Continued)

(52) U.S. Cl.
CPC ... *A61M 25/10184* (2013.11); *A61B 17/1204* (2013.01); *A61B 17/12031* (2013.01); *A61B 17/12036* (2013.01); *A61B 17/12045* (2013.01); *A61B 17/12109* (2013.01); *A61B 17/12136* (2013.01); *A61M 25/10* (2013.01); *A61M 25/1002* (2013.01); *A61M 25/1011* (2013.01); *A61M 25/10187* (2013.11);
(Continued)

(58) Field of Classification Search
CPC .............. A61M 25/10; A61M 25/1002; A61M 25/1011; A61M 25/10184; A61M 25/10187; A61B 17/12031; A61B 17/12036; A61B 17/12109; A61B 17/12136; A61B 17/1204; A61B 17/12045
See application file for complete search history.

(56) References Cited

U.S. PATENT DOCUMENTS 2,676,586 A    4/1954   Coakwell, Jr.
3,585,983 A    6/1971   Kautrowitz
(Continued)

FOREIGN PATENT DOCUMENTS

EP    0 203 310 A2    3/1986
EP    1 891 902 A1    2/2008
(Continued)

OTHER PUBLICATIONS

Wikipedia; "Pulmonary artery catheter Pulmonary artery catheter", Wikipedia, The Free Encyclopedia., May 12, 2012, XP055235920, Retrieved from the Internet:URLhttps://en.wikipedia.org/w/index.php?title=Pulmonary_artery_catheter&oldid+694424669 [retrieved on Feb. 17, 2017] (5 pages).
(Continued)

*Primary Examiner* — Tuan V Nguyen
(74) *Attorney, Agent, or Firm* — J. Bennett Mullinax, LLC

(57) ABSTRACT

A system for use in prevention of stroke is provided that has a shaft that carries an occluding balloon. The occluding balloon is inflated to occlude blood flow through at least one of a right carotid artery and a left carotid artery. An actuation device for causing inflation of the occluding balloon is present. The inflation is applied in a cyclical nature based upon a cardiac cycle. The cyclical inflation of the occluding balloon in turn causes a resulting cyclical occlusion.

14 Claims, 21 Drawing Sheets

Related U.S. Application Data

(60) Provisional application No. 61/838,278, filed on Jun. 22, 2013, provisional application No. 61/668,980, filed on Jul. 6, 2012.

(51) Int. Cl.
*A61B 17/12* (2006.01)
*A61B 17/22* (2006.01)
*A61M 25/00* (2006.01)

(52) U.S. Cl.
CPC ............ *A61B 2017/12127* (2013.01); *A61B 2017/22067* (2013.01); *A61M 25/1018* (2013.01); *A61M 2025/0003* (2013.01); *A61M 2025/1045* (2013.01); *A61M 2025/1052* (2013.01); *A61M 2210/12* (2013.01); *A61M 2230/04* (2013.01); *A61M 2230/30* (2013.01)

(56) References Cited

U.S. PATENT DOCUMENTS

| | | | |
|---|---|---|---|
| 3,587,584 | A | 6/1971 | Bourbon |
| 4,395,806 | A | 8/1983 | Wonder |
| 4,676,232 | A | 6/1987 | Olsson et al. |
| 4,745,924 | A | 5/1988 | Ruff |
| 4,984,563 | A | 1/1991 | Renaud |
| 5,059,177 | A | 10/1991 | Towne |
| 5,271,409 | A | 12/1993 | Millay |
| 5,360,403 | A | 11/1994 | Mische |
| 5,441,051 | A | 8/1995 | Hileman |
| 5,514,079 | A | 5/1996 | Dillon |
| 5,741,295 | A | 4/1998 | McEwen |
| 6,156,005 | A | 12/2000 | Theron |
| 6,325,067 | B1 | 12/2001 | Sterman et al. |
| 6,425,916 | B1 * | 7/2002 | Garrison ............... A61F 2/2418 623/1.26 |
| 6,595,980 | B1 | 7/2003 | Barbut |
| 7,250,025 | B2 | 7/2007 | Nigroni |
| 7,374,531 | B1 | 5/2008 | Kantrowitz |
| 7,458,980 | B2 | 12/2008 | Barbut |
| 7,727,254 | B2 | 6/2010 | Pab |
| 7,972,356 | B2 | 7/2011 | Boyle et al. |
| D643,536 | S | 8/2011 | Vivenzio |
| 7,998,104 | B2 | 8/2011 | Chang |
| 8,025,674 | B2 | 9/2011 | Barbut et al. |
| 8,034,043 | B1 | 10/2011 | Barbut |
| 8,061,562 | B2 | 11/2011 | Carpenter |
| 8,062,324 | B2 | 11/2011 | Shimon et al. |
| 2002/0115982 | A1* | 8/2002 | Barbut ............... A61B 5/0215 604/509 |
| 2002/0173815 | A1 | 11/2002 | Hogendijk et al. |
| 2005/0015048 | A1 | 1/2005 | Chiu |
| 2005/0075531 | A1 | 4/2005 | Loeb et al. |
| 2005/0154344 | A1 | 7/2005 | Chang |
| 2005/0197624 | A1 | 9/2005 | Goodson |
| 2009/0326575 | A1 | 12/2009 | Galdonik |
| 2010/0179583 | A1 | 7/2010 | Carpenter et al. |
| 2010/0324589 | A1 | 12/2010 | Carpenter et al. |
| 2011/0028934 | A1 | 2/2011 | Buckman et al. |
| 2011/0054322 | A1 | 3/2011 | Zanatta |
| 2011/0295114 | A1 | 12/2011 | Agah et al. |
| 2011/0313445 | A1 | 12/2011 | Galdonik |
| 2012/0179195 | A1 | 7/2012 | Lashinski |
| 2012/0203265 | A1 | 8/2012 | Heuser |
| 2013/0023909 | A1 | 1/2013 | Duhay |
| 2013/0164742 | A1 | 7/2013 | Ganesan et al. |
| 2014/0024955 | A1 | 1/2014 | Zhadkevich |
| 2014/0336690 | A1 | 11/2014 | Zhadkevich |

FOREIGN PATENT DOCUMENTS

| | | |
|---|---|---|
| EP | 2 260 776 A1 | 12/2010 |
| EP | 2 682 154 A1 | 1/2014 |
| WO | WO 98/47558 | 6/1998 |
| WO | WO 99/36028 | 7/1999 |
| WO | WO 00/32266 A1 | 6/2000 |
| WO | WO 01/13983 A2 | 3/2001 |
| WO | WO 2010/081025 A1 | 7/2010 |
| WO | WO 2011/017103 A2 | 2/2011 |
| WO | WO 2011/068946 A1 | 2/2011 |
| WO | WO 2012/083227 A1 | 6/2012 |

OTHER PUBLICATIONS

Joe Elbery; "Swan Ganz Physiology"; You Tube video retrieved from https://www.youtube.com/watch?v=7putxZNij4; Jan. 21, 2012; copyright 2012; published by Edwards Lifesciences, Irvine, California, USA; (2 page screen shot included).

Various Anonymous Authors; "Circle of Willis"; Wikipedia article retrieved from https://en.wikipedia.org/wiki/Circle_of_Willis; retrieved on Nov. 8, 2016; pp. 1-4; copyright 2016 Wikipedia Foundation Inc.; San Francisco; California; USA; (4 pages).

European Patent Office; Extended European Search Report; European Application No. 14166170.2-1654; European Patent Office; pp. 1-7; publisher European Patent Office; Published Munich, Germany; copyright and dated Jul. 28, 2014; (7 pages).

European Patent Office; Extended European Search Report; European Application No. 13175517.5-1506; European Patent Office; pp. 1-10; publisher European Patent Office; Published Berlin, Germany; copyright and dated Oct. 7, 2013; (9 pages).

* cited by examiner

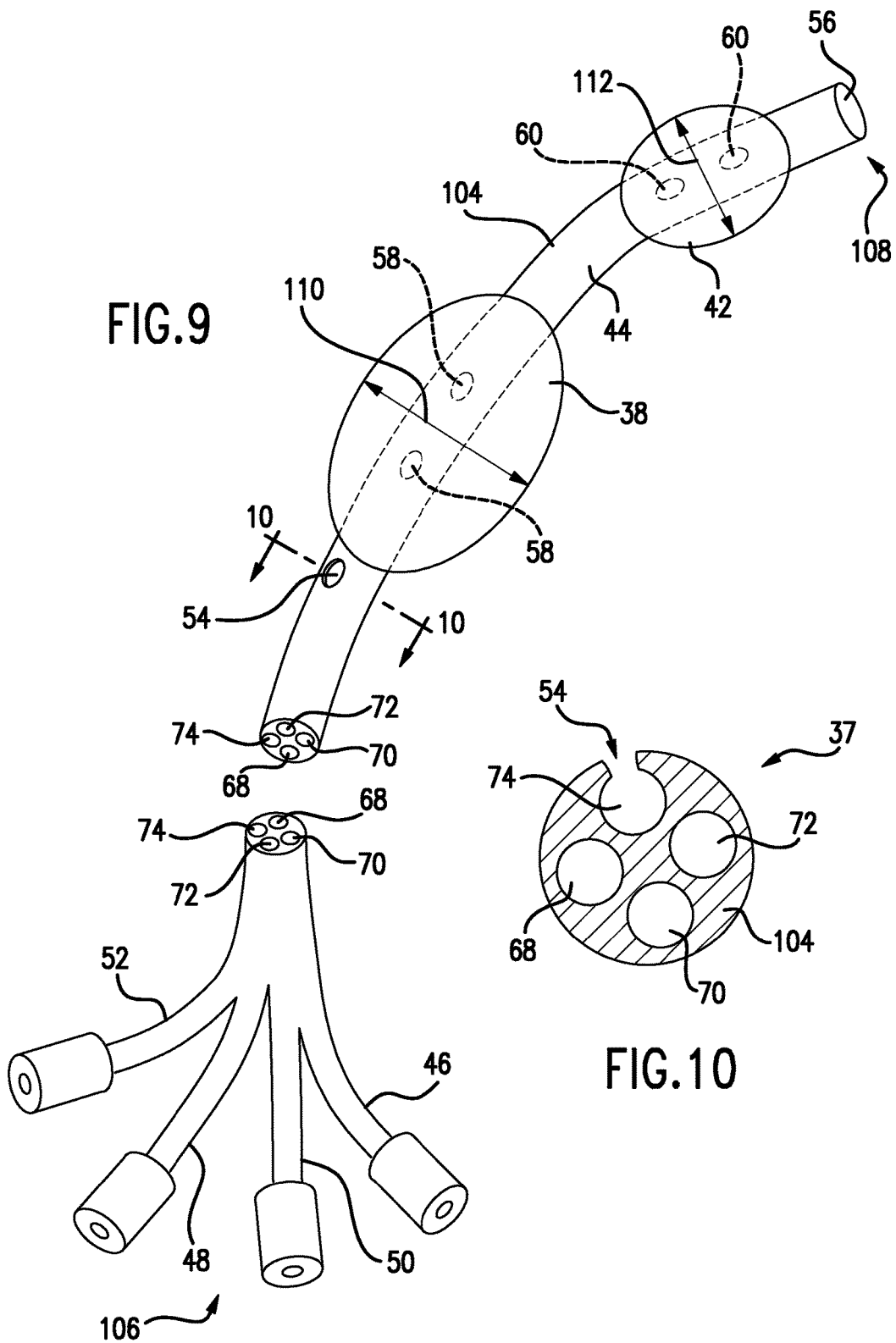

OCCLUDING CATHETER AND DYNAMIC METHOD FOR PREVENTION OF STROKE

CROSS REFERENCE TO RELATED APPLICATIONS

This application claims the benefit of and is a continuation-in-part of U.S. application Ser. No. 13/918,492 filed on Jun. 14, 2013 and entitled, "Occluding Catheter and Method for Prevention of Stroke" that issued as U.S. Pat. No. 9,498,225 on Nov. 22, 2016. U.S. Pat. No. 9,498,225 is a non-provisional and claims the benefit of U.S. Application Ser. No. 61/668,980 filed on Jul. 6, 2012 and entitled, "Device and method of prevention of embolic stroke." This patent also claims the benefit of and is a non-provisional of U.S. Application Ser. No. 61/838,278 filed on Jun. 22, 2013 and entitled, "Vascular Occlusion Device." U.S. application Ser. Nos. 13/918,492, 61/668,980, and 61/838,278 are incorporated by reference herein in their entireties for all purposes.

FIELD OF THE INVENTION

The present invention relates generally to devices and methods for the prevention of stroke. More particularly, the present application involves a pressurized vascular occlusion device that may induce temporary dynamic endovascular occlusion of blood flow to cerebral vessels with divergence of emboli downstream from cerebral circulation.

BACKGROUND

Intraoperative embolic stroke is one of the most dreadful complications of cardiac, aortic and vascular procedures, diagnosed in 1-22% of patients undergoing cardiovascular surgery. Even more frequently, in up to 70% of cases, patients undergoing heart, valve, coronary artery bypass and aortic surgery experience subclinical embolic events as recorded by transcranial Doppler and MRI. These embolic events lead to cognitive impairment and disability and have a significant impact on patients' recovery.

The main sources of cerebral emboli and stroke in this setting reside in the heart, heart valves, thoracic aorta, and great vessels when these structures are intervened thereon. Even simple cardiac catheterization with an endovascular catheter can induce microtrauma of the atherosclerotic thoracic aorta leading to formation of embolic particles with subsequent embolic brain injury ranging from latent ischemic foci to a massive or even fatal stroke.

Multiple devices are known that attempt to prevent embolization of the carotid arteries during endovascular and cardiac interventions. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, including aortic dissection, bleeding, thrombosis, and carotid cerebral embolization and stroke.

One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to aortic wall and acute aortic dissection.

Another such device for preventing emboli into the cerebral circulation includes a porous deflector/intra-aortic shield that captures or diverts potential emboli into the distal vasculature. A yet additional device has also been proposed for use during aortic valve surgery and is an intra-aortic filter catheter that captures emboli during this procedure. These devices also introduce complex and bulky hardware into the lumen of the aorta and are thus associated with the same set of complications that can be seen with any endovascular surgery such as aortic wall trauma, dissection, thrombosis, bleeding, emboli and stroke. It has been established that intravascular filters are not able to capture emboli smaller than the pore size of the available devices (currently 60-140 μm) resulting in cerebral microembolization. Embolization may also occur due to poor apposition of the filter to the aortic or carotid arterial wall.

Furthermore, the placement of the filter by itself may produce cerebral emboli. For example, the mere passing of a guide wire into a carotid artery generates approximately 40,000 microemboli, with a significant percentage of small, less than 60 μm, particles that are not retained by standard filters. Therefore, in spite of multiple innovations in the field of anti-embolic devices, the problem of cerebral emboli and stroke during cardiovascular surgery is far from being resolved.

It is known to use balloon occlusion catheters for the prevention of embolic stroke. In this regard, the balloon occlusion catheter is placed inside of one of the carotid arteries when a procedure, for example carotid angioplasty and stenting, is conducted on the carotid artery in question. These devices only block flow on one, but not both, of the carotid arteries. Although capable of preventing stroke when a single carotid artery is operated upon, this device cannot work to prevent stroke during procedures on the heart and aorta, endovascular or open, and cannot provide for bilateral occlusion. This device cannot simultaneously occlude both the left and right carotid arteries to prevent flow simultaneously through both of these arteries, and thus cannot prevent stroke should emboli flow into the non-blocked carotid artery. These devices were not designed to assure a dynamic functional protection of the cerebral circulation depending upon the phase of the cardiac cycle.

Prior designs of carotid balloon catheters were not made to protect both right and left cerebral hemispheres from cardiac and aortic emboli. Their shape, design and method of use were specifically crafted for a single purpose of protecting the brain hemisphere on the side of carotid intervention only, either ipsilaterally or unilaterally. Known carotid balloon catheters do not have an orientation or positioning that corresponds to an average location of the orifices of the innominate, subclavian, and common carotid arteries.

Further, known endovascular carotid occluding devices require a guide wire to be inserted into the carotid arterial system. This procedure by itself is known to induce carotid trauma and cause the formation of cerebral emboli and resultant stroke. Still additionally, prior endovascular carotid occluding devices are not capable of reducing arterial flow through both right and left vertebral arteries, either at the same time or individually. This deficiency may allow emboli to enter vertebrobasilar circulation and cause stroke. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGS. in which:

FIG. 9 is a perspective view of the occluding catheter of FIG. 2 in an inflated state and with a section cut away to view interior portions.

FIG. 10 is a cross-sectional view taken along line 10-10 of FIG. 9.

Figure 1:
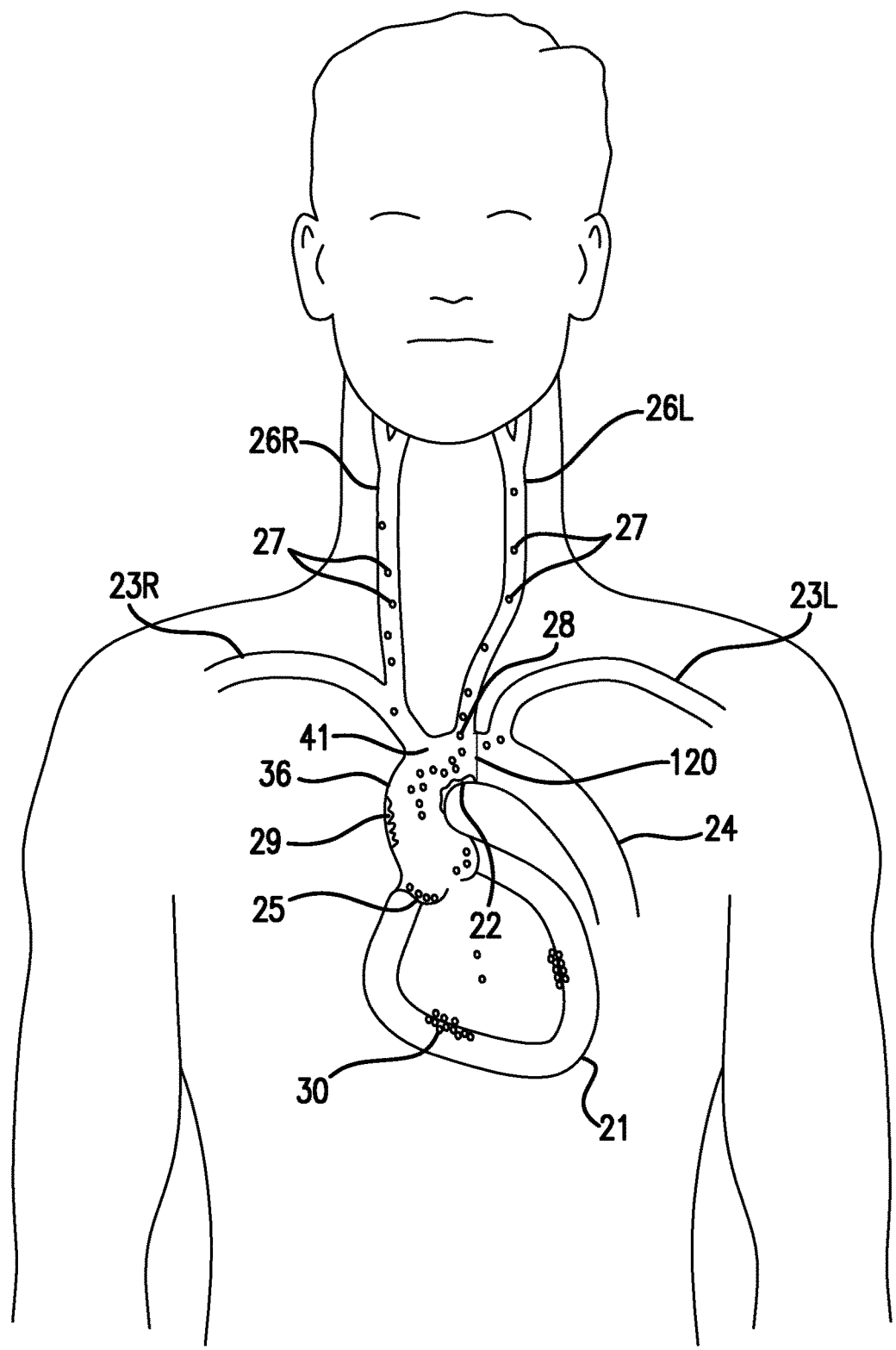
FIG. 1 is a front view of a patient with emboli in the heart and ascending thoracic aorta with subsequent propagation of emboli into both carotid arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an occluding catheter 37 that may be introduced into the circulatory system of a patient in order to prevent emboli 28 from entering the carotid arteries 26R, 26L and causing stroke. The occluding catheter 37 may be arranged so that it has one occluding balloon 38, or a pair of occluding balloons 38 and 42, or three or more occluding balloons in accordance with different exemplary embodiments. The occluding catheter 37 can be positioned within the circulatory system in a deflated state. When needed, the occluding catheter 37 can be inflated in order to block blood flow through the carotid arteries 26R, 26L and hence prevent emboli 28 from flowing through the carotid arteries 26R, 26L and into cerebral circulation. The occluding catheter 37 can be equipped with the capability of employing a guide wire 100 and with the ability to measure pressure downstream in one or more arteries of the patient to ensure proper blockage. If needed or desired, flow may be blocked through both vertebral arteries. An associated method for preventing emboli 28 from entering cerebral circulation is also provided.

With reference to FIG. 1, a front view of a patient is shown in which emboli 28 are transferred from the aortic arch 22 into the carotid arteries 26R, 26L. The emboli 27 that are present in the carotid arteries 26R, 26L can then be transferred into the cerebral circulation causing stroke of the patient. The emboli 27 may be fragments of atherosclerotic plaque 29 of the ascending aorta 36 that become dislodged during manipulation of the ascending thoracic aorta 36. Also shown in FIG. 1 is calcification of the aortic valve 25 and intracardiac emboli 30 of the heart 21 that can also be the origin of emboli 27 eventually present in the carotid arteries 26R, 26L. The intracardiac emboli 30 may include air, gas, thrombi and atherosclerotic materials. Although all of the various emboli in the heart 21, aortic arch 22, ascending aorta 36, and aortic valve 25 need not be present in all instances, they are all shown in FIG. 1 for sake of example. Trauma to the heart 21, aortic valve 25 and aortic structures during placement and removal of items such as aortic clamps and electrophysiological instruments, along with manipulations such as coronary artery bypass grafting, aortic and mitral valve replacement, catheter ablation, endovascular grafting of the aorta 22, balloon valvuloplasty percutaneous implantation of the aortic or mitral valves, endovascular manipulations on the aorta 22, aortic branches and the heart 21 may give rise to the presence of emboli 27 in the carotid arteries 26R, 26L. Critical moments of the aforementioned procedures (for example during the aortic cross clamp manipulation, percutaneous aortic and mitral valvuloplasty or valve implantation, coronary interventions, endovascular grafting of the aorta 22 and its branches, and endovascular procedures on the aorta 22) may cause emboli 27 to form and cause stroke and are referred to as "emboligenic" events.

Figure 2:
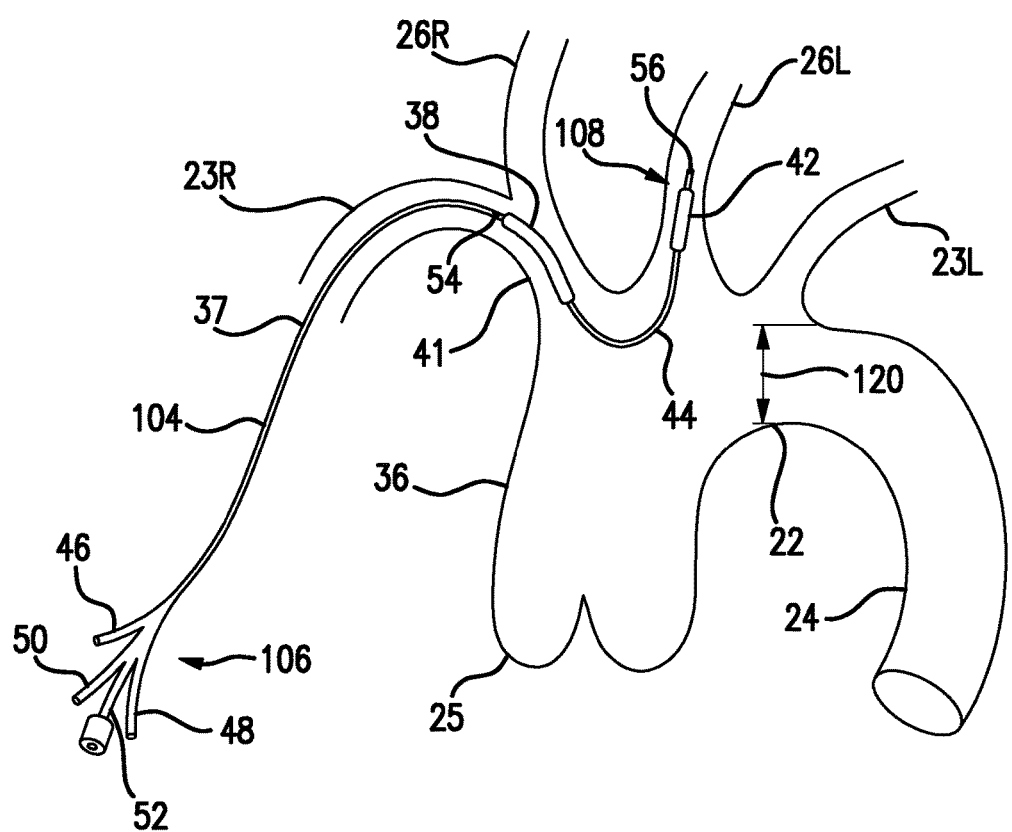
FIG. 2 is a front view of the patient with an occluding catheter in a deflated state positioned within the circulatory system of the patient.

FIG. 2 discloses an occluding catheter 37 positioned within the circulatory system of the patient. The occluding catheter 37 is introduced through a right subclavian artery 23R and has a shaft 104 with a proximal end 106 located outside of the patient, and a distal end 108 positioned within the left carotid artery 26L. The occluding catheter 37 has a proximal occluding balloon 38 located closer to the health care provider and thus closer to the proximal end 106 than a distal occluding balloon 42 which is farther away from the health care provider and thus closer to the distal end 108. The proximal occluding balloon 38 may be located within an innominate artery 41 of the patient. The occluding catheter 37 can be arranged as shown in FIG. 2 so that no portion of it is located within the right carotid artery 26R. In other exemplary embodiments, some portion of the occluding catheter 37 may be located within the right carotid artery 26R. A segment 44 of the shaft 104 that is located between the proximal and distal occluding balloons 38, 42 may be located in the aortic arch 22.

The occluding catheter 37 may be inserted into the right subclavian artery 23R via right radial, brachial, axillary or subclavian artery approach and can be advanced under fluoroscopic and arterial blood pressure guidance into the innominate artery 41, aortic arch 22 and finally into the left carotid artery 26L. The ideal position of the proximal tip of the distal occluding balloon 42 may be in the proximal segment of the left carotid artery 26L, whereas the proximal occluding balloon 38 may reach the level of the innominate artery 41.

The insertion of the occluding catheter 37 may be performed when both the proximal 38 and distal 42 occluding balloons are deflated. However, once the distal occluding balloon 42 reaches the level of the aortic arch 22 it can be inflated to facilitate its advancement into the left carotid artery 26L. The inflated distal occluding balloon 42 is thus naturally propelled forward into the left carotid artery 26L by arterial blood flow. The adequacy of the position of the distal occluding balloon 42 is confirmed with fluoroscopy and, if desired, by appearance of the dampened arterial pressure recorded from the end pressure measurement channel 70 through the end pressure measurement port 50 with its distal tip opening 56 located distal from the tip of the distal occluding balloon 42 downstream from the area of occlusion of the left carotid artery 26L.

Once an adequate position of the distal occluding balloon 42 in the left carotid artery 26L is achieved it may be deflated. A normal arterial blood pressure waveform as recorded from the distal tip opening 56 should reappear to confirm adequate perfusion via the left carotid artery 26L.

Correct placement of the distal occluding balloon 42 within the left carotid artery 26L may result in correct placement of the proximal occluding balloon 38 within the innominate artery 41. This is achieved by choosing an occluding catheter 37 with the longitudinal length of segment 44 between proximal and distal occluding balloons 38, 42 to be slightly larger than the distance between the left carotid artery 26L and innominate artery 41 as estimated by preoperative CT scan. According to some measurements, an optimal length of segment 44 should be 2-6 cm longer than the distance between the innominate artery 41 and the left carotid artery 26L to allow for a smooth turn of the interballoon portion of the occluding catheter 37 within the aortic arch 22. Considering the fact that the average distance between the orifices of the innominate artery 41 and left carotid artery 26L in the normal aortic arch 22 configuration is from 0.5-1.0 cm, the length of segment 44 between the distal and proximal occluding balloons 38 and 42 should lie within the range between 3 and 8 cm. Therefore, in practice several different sizes of the occluding catheter 37 can be constructed where the length of the segment 44 between the proximal 38 and distal 42 occluding balloons vary from 3 to 12 cm, or from 0.5 to 12 cm, or from 2 to 2.5 cm in various embodiments. The diameter, volume and length of the occluding balloons 38, 42 may also vary according to the patient's anatomy with the proximal occluding balloon 38 being 50-100% longer and larger than its distal 42 counterpart. The length of segment 44 may be selected so that the proximal occluding balloon 38 is located within the innominate artery 41 at the same time that the distal occluding balloon 42 is located within the left carotid artery 26L.

The next step in the method of using the occluding catheter 37 may be the inflation of the proximal occluding balloon 38 in the lumen of the innominate artery 41 and the recording of post-occlusion pressure in the distal innominate artery 41. This pressure may be recorded via an opening 54 of the shaft 104 located downstream from the proximal occluding balloon 38 in the direction of arterial blood flow. An intermediate pressure measurement channel 74 is in communication with the opening 54 and with an intermediate pressure measurement port 52 at the proximal end 106. This port 52 can be used to confirm an adequate position of the proximal occluding balloon 38 by the appearance of the dampened waveform. Once the pressure measurement indicates that the proximal occluding balloon 38 is properly positioned, the proximal occluding balloon 38 can be deflated and the occluding catheter 37 is considered ready for use. The interruption of carotid flow or pulse may be assessed by angiography, carotid Doppler, or arterial pressure and waveform patterns distal to the level of occlusion in accordance with certain exemplary embodiments. In addition, percutaneous cerebral oximetery, electroencephalography and transcranial Doppler monitoring can be applied. In other arrangements, it may not be the case that this monitoring is applied in order to confirm positioning of the proximal and distal occluding balloons 38, 42.

Figure 3:
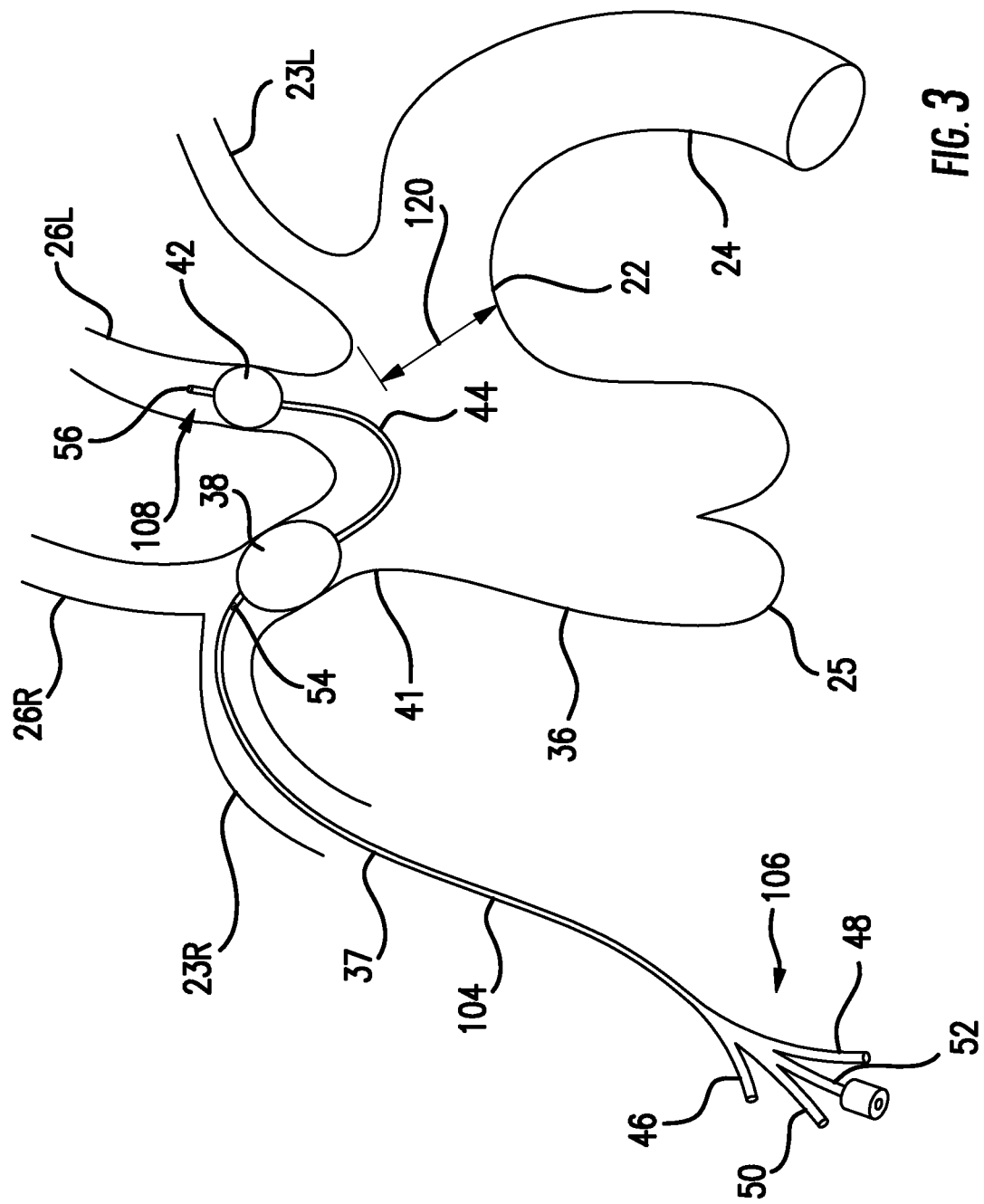
FIG. 3 is a front view of the patient of FIG. 2 with the occluding catheter in an inflated state.

The proximal and distal occluding balloons 38, 42 may be inflated such that they are both inflated at the same time as shown with reference to FIG. 3. Simultaneous inflation may lead to temporary interruption of the carotid arterial flow, preventing all potential emboli 28, released due to manipulations on atherosclerotic calcified plaques 29 of the ascending aorta 36 (or from other such emboligenic events) from entering the cerebral circulation, and diverging them downstream from the cerebral circulation into the descending aorta 24, thus protecting the patient from embolic stroke. The occluding balloons 38, 42 may be inflated to such a pressure and be of such a resiliency that they completely block any blood flow past them and through the particular artery or arteries into which they are positioned. However, it is to be understood that other arrangements are possible in which some amount of blood may flow past the proximal occluding balloon 38 and/or the distal occluding balloon 42.

Figure 4:
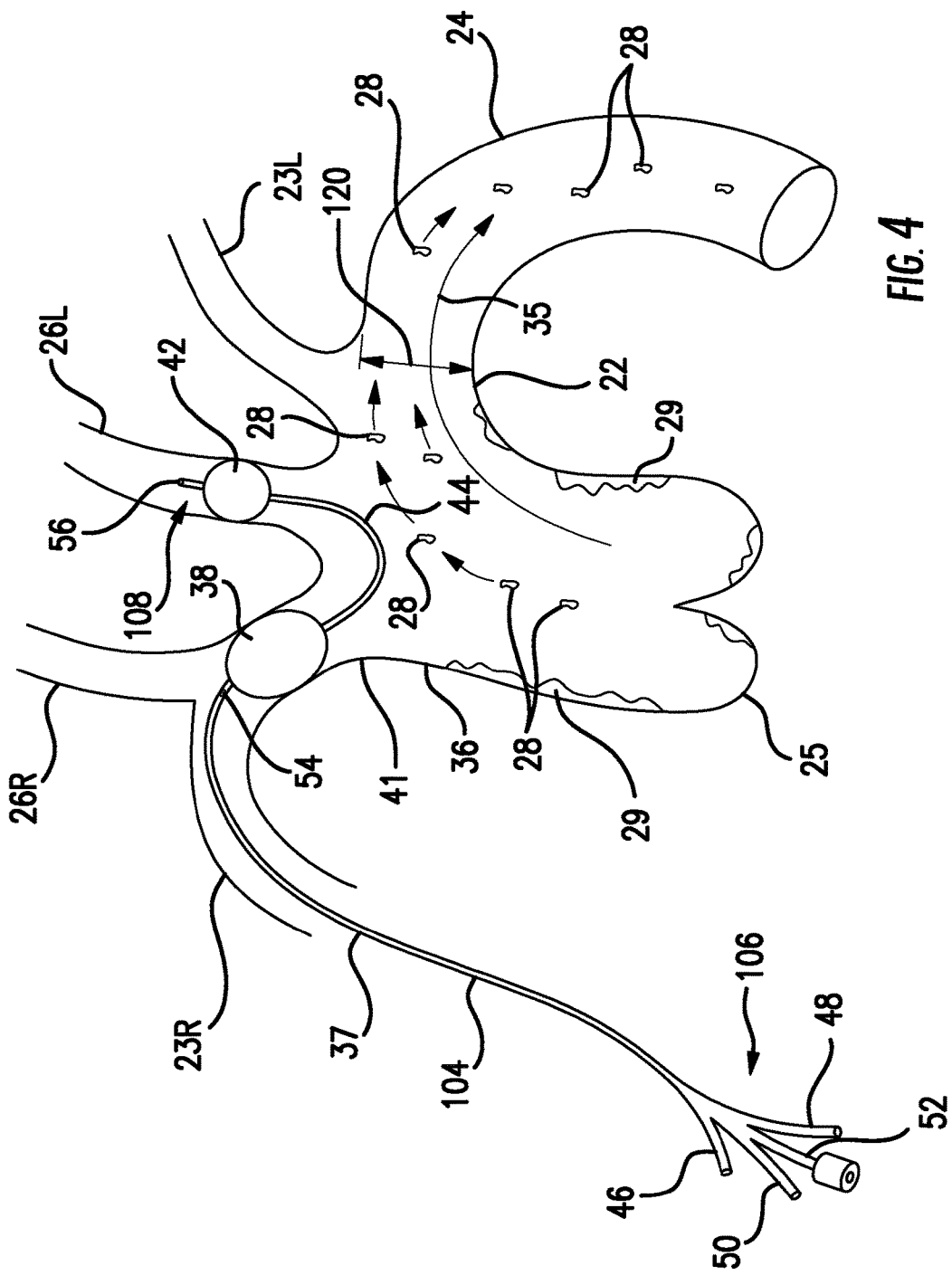
FIG. 4 is a front view of the patient of FIG. 3 that shows the divergence of emboli.
Figure 5:
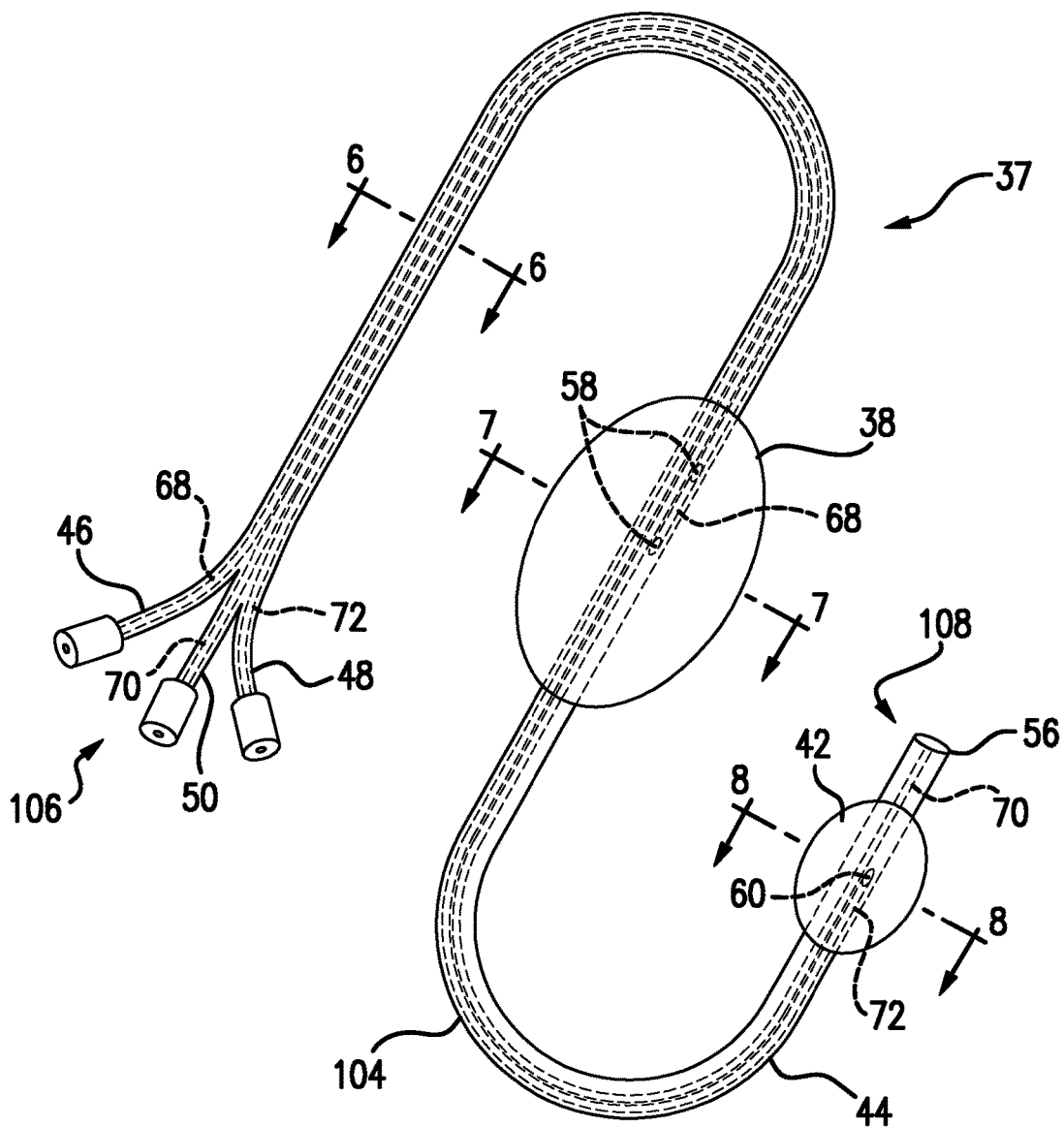
FIG. 5 is a front view of an occluding catheter in accordance with one exemplary embodiment in an inflated state.
Figure 6:
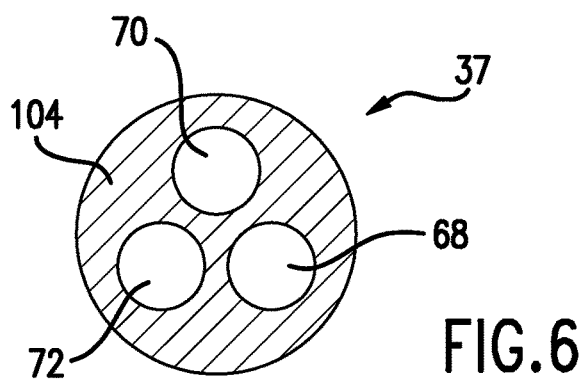
FIG. 6 is a cross-sectional view taken along line 6-6 of FIG. 5.
Figure 7:
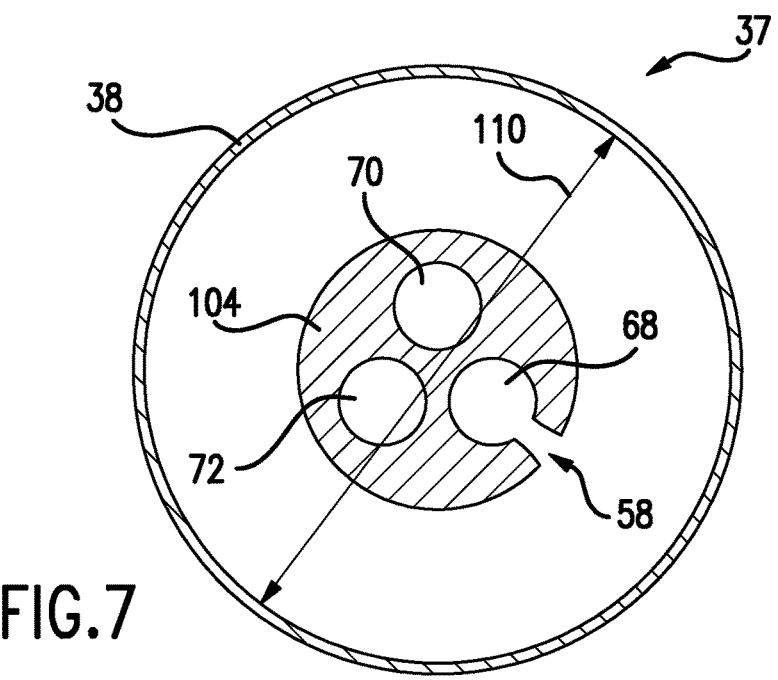
FIG. 7 is a cross-sectional view taken along line 7-7 of FIG. 5.
Figure 8:
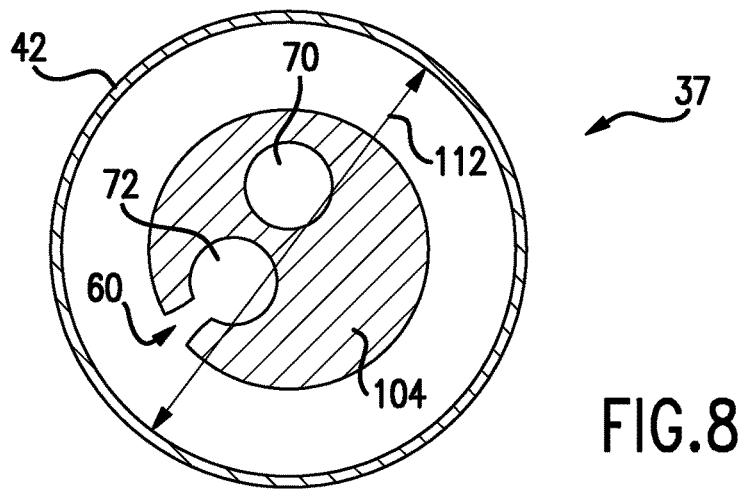
FIG. 8 is a cross-sectional view taken along line 8-8 of FIG. 5.

FIG. 4 illustrates the flow of blood in the circulatory system upon inflation of the proximal and distal occluding balloons 38 and 42. Temporary interruption of flow at the level of the proximal carotid arteries 26R, 26L leads to divergence of blood flow 35 carrying all potential cerebral emboli 28 into the descending aorta 24. Emboli 28 diverted from cerebral circulation move through the descending aorta 24. The proximal occluding balloon 38 may completely block the innominate artery 41 so that no blood flow or emboli 28 may be transferred through the right carotid artery 26L and the right subclavian artery 23R. The position of the proximal occluding balloon 38 can be made so that it is right at the bifurcation of the innominate artery 41 in order to completely occlude the orifice of the right carotid 26R and right subclavian 23R arteries at the same time.

Both distal and proximal occluding balloons 38, 42 are inflated just before proceeding with the part of the procedure prone to generate cerebral emboli 27. This may be the placement or removal of an aortic cross clamp, implantation of valves, endovascular grafts and stents, or other procedures outlined above. The balloon pressure required to completely interrupt flow in carotid arteries 26R, 26L at this point of intervention is usually significantly less and rarely exceed 50 mm of mercury. This consideration is based on the fact that the physician may bring the systemic perfusion pressure of the patient to minimal levels at this particular time of the procedure that involves the emboligenic event. Therefore, the occluding balloon 38, 42 pressure required to occlude carotid arteries 26R, 16L at this short period of time can be significantly lower and less damaging to the carotid arterial walls 26R, 26L.

Inflation of the occluding balloons 38, 42 can be such that they are inflated to a pressure exceeding the patient's systemic pressure by 10-20 mm Hg or more just before proceeding with the emboligenic part of the procedure. Adequate occlusion of the carotid arteries 26R and 26L will lead to a known phenomenon of a temporary reduction of flow through vertebral arteries leading to additional divergence of blood and emboli 28 away from both vertebral arteries. This will decrease the risk of stroke in vertebro-basilar circulation. Insertion of the occluding catheter 37 through the right side and inflation of the proximal occluding balloon 38 at the level of the innominate artery 41 may preclude entrance of emboli 28 into the right subclavian artery 23R and right vertebral arterial system. Insertion of the occluding catheter 37 through the left side of the patient may cause the proximal occluding balloon 38 to be at the level of the left subclavian artery 23L to preclude entrance of emboli into the left subclavian artery 23L and left vertebral arteries, and the distal balloon 32 to be at the level of the innominate artery 41, to preclude entrance of emboli into the right carotid 26R, right subclavian 23R and right vertebral arteries, further reducing the risk of embolic stroke.

The distal and proximal occluding balloons 38, 42 may be deflated 30-90 seconds after this part of the procedure is completed to achieve complete washout of all potential emboli 28 into the descending aorta 24 and distal vasculature, while avoiding migration of emboli 28 into the carotid arteries 26R and 26L. This timing, however, can be either shortened or extended depending on multiple factors that comprise the timing of embolic events, their intensity and the degree of patient's tolerance to transient interruption of cerebral flow such as the degree of hypothermia and the condition of the collateral cerebral flow as measured by EEG, transcranial Doppler, or other means.

The length of most manipulations associated with a transgression of emboli into cerebral circulation rarely exceed 1-2 minutes. Temporary interruption of the carotid flow for this period of time, plus 0.5-1.5 min to allow for complete washout of emboli 28 from the aorta 22 is completely safe and feasible.

Partial deflation of the balloons 38, 42 may provide necessary blood flow to the brain while still decreasing the degree of cerebral embolization. The technology will allow one to extend the length of cerebral protection from embolic stroke while assuring cerebral perfusion.

Once the emboligenic procedure is completed both occluding balloons 38 and 42 may be deflated. Optionally, repeating the whole process of cerebral protection may be conducted if desired once a 5-10 min period of cerebral reperfusion is reached. The procedure can be repeated at any time of surgery and on multiple occasions when the emboligenic intervention is anticipated. Upon completion of the main surgical procedure, the occluding catheter 37 can be completely removed or pulled back completely into the right subclavian artery 23R for later removal.

FIGS. 5-8 illustrate an exemplary embodiment of the occluding catheter 37 as being a 3-lumen, 2-balloon catheter 37. The occluding catheter 37 includes a shaft 104 that may have an outer circumference that is circular in cross-sectional shape. However, other cross-sectional shapes of the outer circumference are possible in accordance with other exemplary embodiments. Ports 46, 48 and 50 may have openings at their extreme proximal ends to allow for communication with their respective channels 68, 70, 72 and can have fittings configure to receive inflation syringes, pressure measurement devices, guide wires 100 or other components. Channels 68, 70, and 72 have circular cross-sectional shapes and are all the same diameter. However, in other arrangements the cross-sectional shapes may be different and their diameters can be variously sized such that they are not the same size as one another.

The channels 68, 70 and 72 are not in fluid communication with one another. The proximal and distal occluding balloons 38, 42 may be inflated separately from one another such that one is inflated before another one, or such that both inflate simultaneously. Pressure of inflation supplied by a pressure supply 126 may be to a degree greater than the patient's systemic arterial pressure. The pressure inside the occluding balloons 38, 42 may exceed only minimally the patient's systemic and carotid arterial 26R, 26L pressures with the goal to achieve complete interruption of the antegrade carotid flow without undue trauma to these vessels 26R, 26L.

Proximal occluding balloon inflation port 46 is in fluid communication with the proximal occluding balloon channel 68. The channel 68 may terminate at the proximal occluding balloon 38 and may not extend past the proximal occluding balloon 38 in the distal direction. One or more openings 58 may extend through the shaft 104 in order to place the channel 68 into fluid communication with the interior of the proximal occluding balloon 38. Fluid pressure supplied by a syringe or other source may be introduced through port 46, channel 68 and out of opening 58 in order to inflate the proximal occluding balloon 38 to its inflated state.

The proximal occluding balloon 38 may be connected on its distal and proximal ends to the shaft 104 and inflation pressure will cause the proximal occluding balloon 38 to expand so as to have a circular cross-sectional shape. The proximal occluding balloon 38 may have other cross-sectional shapes in other exemplary embodiments such as oval or elliptical. The occluding balloon 38 may be variously shaped and sized in accordance with different exemplary embodiments. The proximal occluding balloon 38 may be coaxial with the shaft 104. In accordance with various embodiments, the proximal occluding balloon 38 may be coaxial with the channel 70, 72 or 68. In other embodiments the proximal occluding balloon 38 is not coaxial with the shaft 104 or any of the channels 70, 72 or 68.

The shaft 104 continues in the distal direction past the proximal occluding balloon 38 but only channels 70 and 72 are present past the proximal occluding balloon 38. The distal occluding balloon 42 is located at the distal end 108 of the shaft such that a segment 44 of the shaft 104 is present between the occluding balloons 38, 42 to space them from one another. The distal occluding balloon channel 72 extends from the distal occluding balloon inflation port 48 and terminates at an opening 60 of shaft 104. The distal occluding balloon 42 is attached at its proximal and distal ends to the shaft 104 and is inflated via pressure supplied through port 48, channel 72 and out of opening 60. A single opening 60 may be present, or a plurality of openings 60 may be present through which pressure can be supplied to inflate the distal occluding balloon 42. The distal occluding balloon 42 may have a circular cross-sectional shape, although other cross-sectional shapes are possible in other exemplary embodiments. The longitudinal length of the distal occluding balloon 42 may be less than that of the proximal occluding balloon 38. However, their longitudinal lengths may be the same in other arrangements, or in yet further designs the longitudinal length of the proximal occluding balloon 38 is less than the longitudinal length of the distal occluding balloon 42. The distal occluding balloon 42 may be coaxial with the shaft 104 in certain arrangements, and in other arrangements may be coaxial with channels 70 or 72. In yet other exemplary embodiments, the distal occluding balloon 42 is not coaxial with shaft 104 and is not coaxial with channels 70 or 72.

The diameter 112 of the distal occluding balloon 42 is less than the diameter 110 of the proximal occluding balloon 38. In other exemplary embodiments diameter 110 may be less than diameter 112, or the diameters 110 and 112 may be equal to one another. The diameters 110 and 112 may be the same along the entire longitudinal lengths of the occluding balloons 38, 42, or the diameters 110 and 112 may be different at different points along the longitudinal lengths of the occluding balloons 110 and 112. The diameters 110 and 112 and cross-sectional shapes of the proximal and distal occluding balloons 38, 42 are described when outside of the body of the patient.

The distal occluding balloon channel 72 may terminate proximal to the distal end of the distal occluding balloon 42. Only the end pressure measurement channel 70 may extend distally beyond the distal occluding balloon 42. The distal tip of the shaft 104 terminates at a distal tip opening 56 at its terminal distal end. The shaft 104 extends beyond the distal occluding balloon 42, but in other arrangements, the distal occluding balloon 42 in the inflated state may extend beyond the terminal distal end of the shaft 104 in the distal direction. The end pressure measurement port 50 can be in communication with the end pressure measurement channel 70 that in turn terminates at the distal tip opening 56. The channel 70 in other arrangements may be in fluid communication with one or both channels 68 and 72. Likewise, in yet other exemplary embodiments, channel 70 is not in fluid communication with channels 68 and 72, but channels 68 and 72 are in fluid communication with one another so that the proximal and distal occluding balloons 38, 42 inflate and deflate with one another. Distal tip opening 56 may be used for pressure measurements distal to the distal occluding balloon 42.

FIGS. 9 and 10 illustrate an alternative exemplary embodiment of the occluding catheter 37 that is a four-channel version of the occluding catheter 37. Intermediate pressure measurement channel 74 extends from an intermediate pressure measurement port 52 to an opening 54 of the shaft 104. Opening 54 is located proximal to the proximal occluding balloon 38. The intermediate pressure measurement channel 74 is not in fluid communication with the other channels 68, 70 and 72 of the occluding catheter 37. The intermediate pressure measurement channel 74 may terminate proximal to the proximal occluding balloon 38. The other components of the occluding catheter 37 are the same as described above and their description need not be repeated. A manometer may be connected to the intermediate pressure measurement port 52 to allow recording of blood pressure from the opening 54. If the proximal occluding balloon 38 is located within the innominate artery 41, the opening 54 may be used to detect the dampening of the arterial pressure in the innominate 41 and right carotid artery 26R, after proximal occluding balloon 38 inflation, confirming adequacy of the flow interruption to the right carotid 26R and subclavian arteries 23R.

Figure 11:
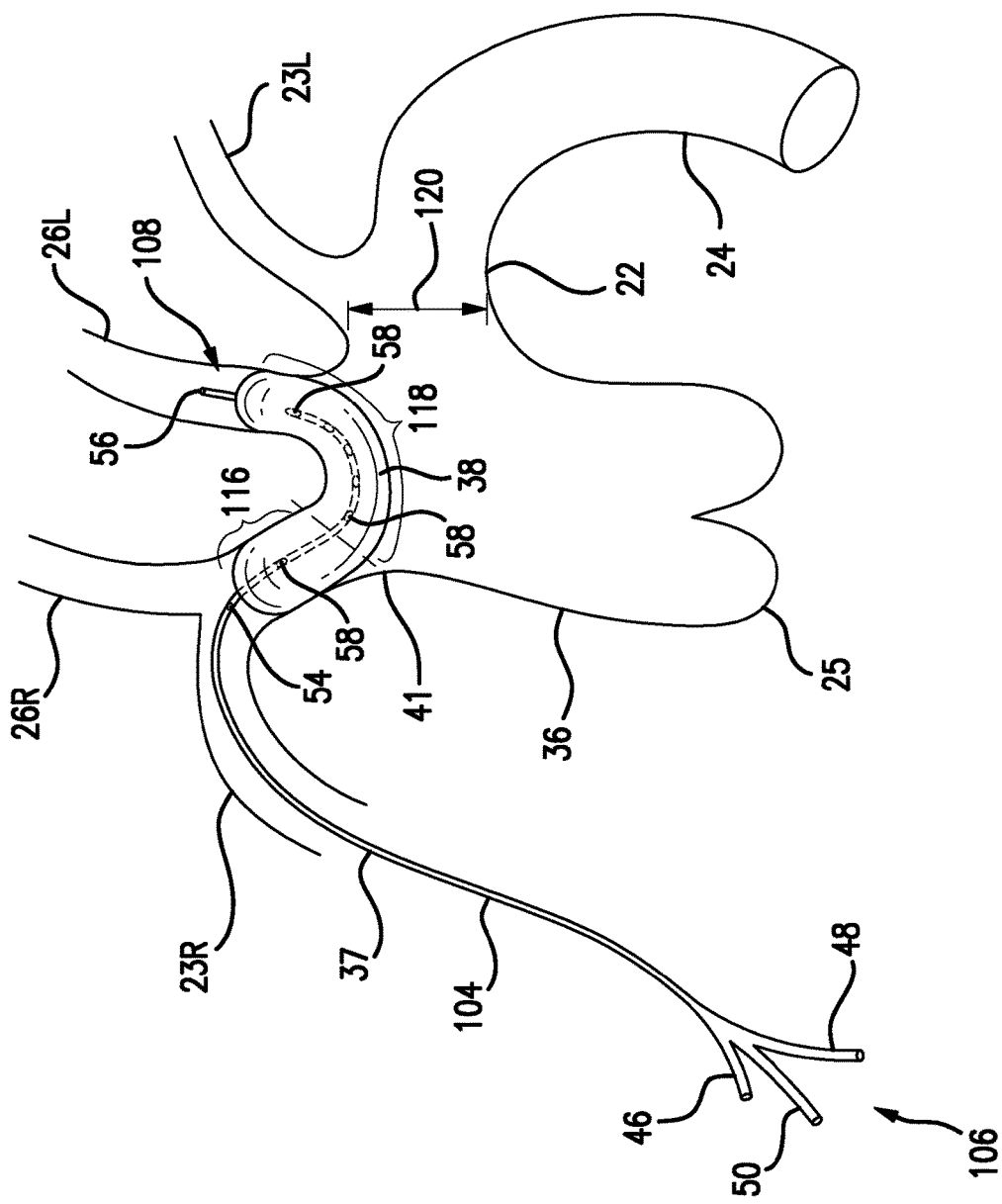
FIG. 11 is a front view of the patient with an inflated occluding catheter in accordance with another exemplary embodiment.

In another embodiment bilateral carotid 23R and 23L flow interruption can be achieved by creating a single occluding balloon 38. FIG. 11 shows one exemplary embodiment with a single occluding balloon 38. The occluding balloon 38 may extend throughout the whole distance between the bifurcation of the innominate artery 41 and the main trunk of the left carotid artery 26L. The single occluding balloon 38 may be longer than both the proximal occluding balloon 38 and distal occluding balloon 42 combined (as described in previous exemplary embodiments), with its length being in the range between 6 and 14 cm. When described as a single occluding balloon 38, it is to be understood that complete blockage of flow through the right and left carotid arteries 26R and 26L may be achieved by the single occluding balloon 38 without the use of any other occluding balloons, or without even the presence of another occluding balloon 38 carried by the occluding catheter 37.

The occluding balloon 38 may be constructed so that it has a proximal portion 116, designated to occlude the innominate artery 41, which is larger than a distal portion 118 of the occluding balloon 38 to assure adequate occlusion of the innominate artery 41. Generally, the innominate artery 41 is at least twice as large as the left carotid artery 26L. The single occluding balloon 38 may thus have a proximal portion 118 with a larger diameter than the diameter of the distal portion 118 of the single occluding balloon 38. These differences in diameters/sizes would be present when the single occluding balloon 38 is inflated without being inside of the patient. The other option involves the single occluding balloon 38 being a large volume, highly compliant occluding balloon that does not have any disparity in the diameters/size of the proximal portion 116 and distal portion 118 when inflated and not inside of the patient. Once inflated inside of the patient and presented with arteries of different sizes, the proximal and distal portions 116, 118 of the highly compliant occluding balloon 38 expand as necessary for complete occlusion of arteries 41 and 26L at minimal pressures and without significant compression of the arterial walls 41, 26L.

The single occluding balloon 38 thus expands as necessary to fill the space required for occlusion as it is a very flexible member in construction.

Figure 12:
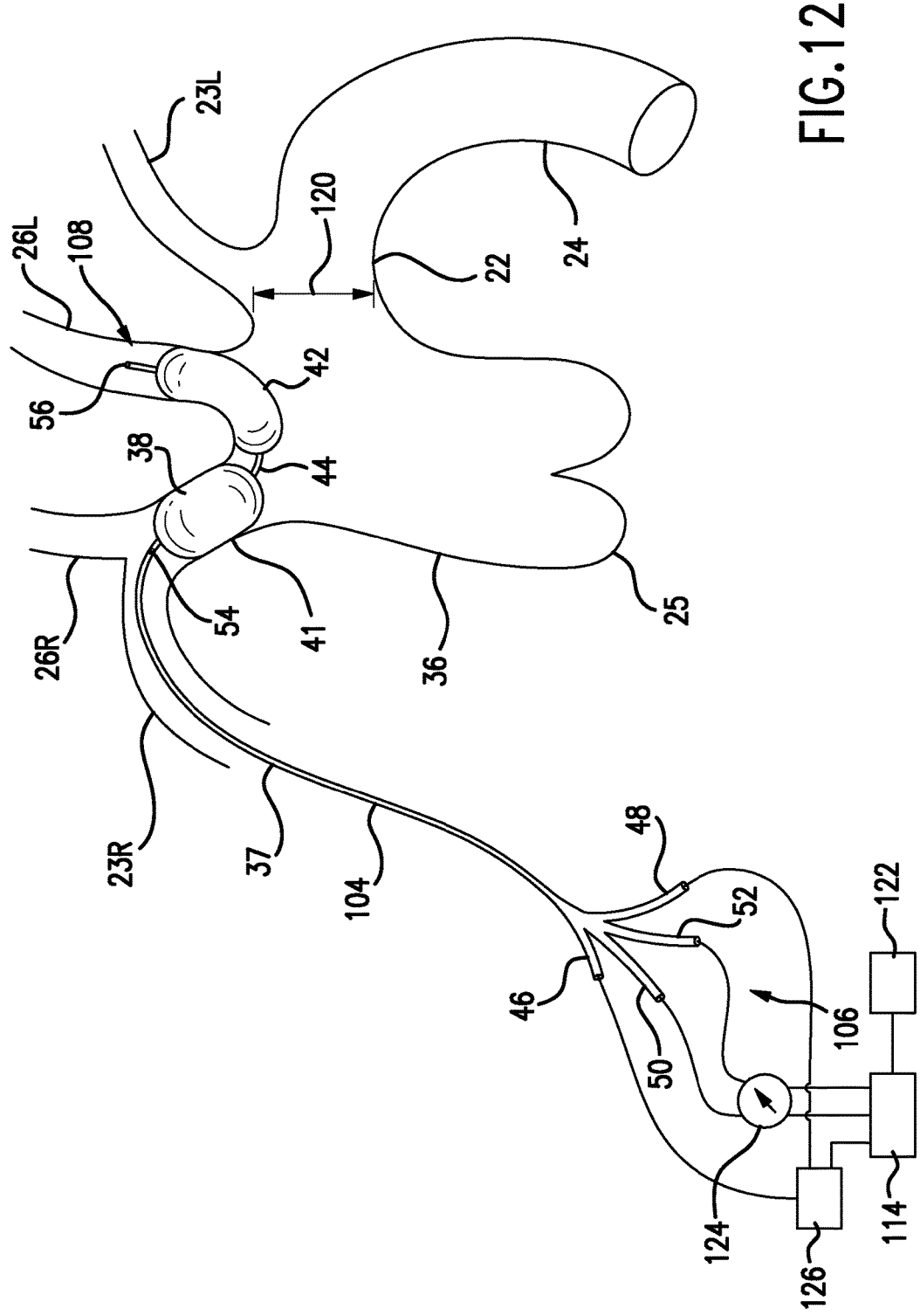
FIG. 12 is a front view of the patient with an inflated occluding catheter and an alarm system in accordance with a further exemplary embodiment.

In order to facilitate the advancement of the occluding catheter 37 in patients with difficult anatomy, a guide wire 100 may be used in one of the channels 70 or 74. With reference to FIG. 12, the guide wire 100 need not be used. Here, the shaft 104 is highly compliant and there is a narrow waist that makes up segment 44. The occluding catheter 37 includes a pair of occluding balloons 38, 42 and segment 44 in the middle of these occluding balloons 38, 42 improves flexibility of the occluding catheter 37. As previously described, separate occluding balloon channels 68 and 72 can be used for separate inflation of the proximal and distal occluding balloons 38 and 42. This allows for selective control of the occlusion of the left carotid artery 26L and innominate arteries 41.

The pair of occluding balloons 38, 42 in FIG. 12 may be rearranged so that they are only a single occluding balloon 38. In this regard, the single occluding balloon 38 will have a proximal portion 116 and a distal portion 118 separated by one another by segment 44 that is not capable of being inflated. A single occluding balloon channel 68 can be used to inflate both the proximal and distal portions 116, 118. Although a single occluding balloon 38 is present, it is divided into two or more portions via uninflated segments such as segment 44 or by various other bands or waists that effect division. Segment 44, when effecting separation of proximal and distal portions 116, 118, achieves better flexibility of the occluding catheter 37 at the level between the two portions 116, 118. This option may allow for an easier passage of the occluding catheter 37 in case of a sharp angle between the innominate artery 41 and left carotid artery 26L. If a pair of occluding balloons 38, 42 are employed the same goal may be achieved by the segment 44. Measurement of arterial pressure and assessing the pressure waveform via the openings 54, 56 before and after inflation will allow confirmation of the adequacy of the flow interruption in the carotid arteries 26L and 26R.

A manometer 124 may be in communication with the end pressure measurement port 50 and the intermediate pressure measurement port 52 to measure pressures at the opening of the shaft 54 (downstream from the proximal occluding balloon 38 in the innominate artery 41 or right subclavian artery 23R) and at the distal tip opening of the shaft 56 (downstream from the distal occluding balloon 42 in the left carotid artery 26L). A pressure supply 126 is in communication with the proximal occluding balloon inflation port 46 and the distal occluding balloon inflation port 48 to provide inflation pressure for the occluding catheter 37. An alarm system 114 is in communication with the pressure supply 126 and manometer 124. Should the physician or physician's assistant forget to deflate the occluding balloons 38, 42 in a timely fashion, an alarm would go off and the occluding balloons 38, 42 would deflate spontaneously to avoid undue interruption of the cerebral flow. The alarm could be also triggered by the occurrence of emboli 27 detected by transcranial Doppler 122 (also in communication with the alarm system 114) or any other means, thus indicating an urgent need for temporary occlusion of the cerebral flow. Here, the alarm system 114 will cause inflation of the occluding balloons 38, 42. The alarm system 114 along with deflation or inflation of the occluding balloons 38, 42 could be overridden by the physician when clinically indicated.

Figure 13:
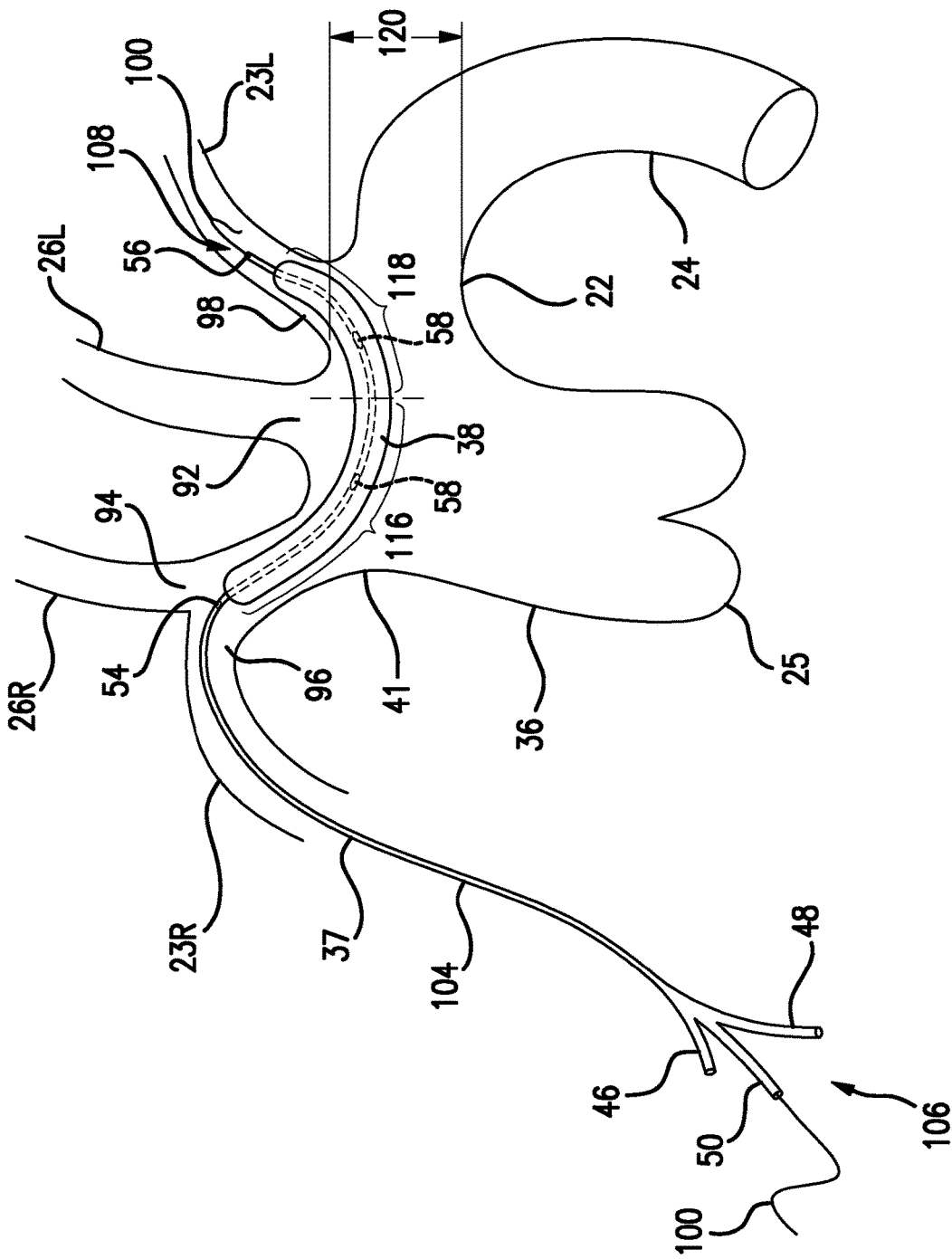
FIG. 13 is a front view of the patient with a deflated occluding catheter introduced through the arteries of the right arm in accordance with another exemplary embodiment.
Figure 14:
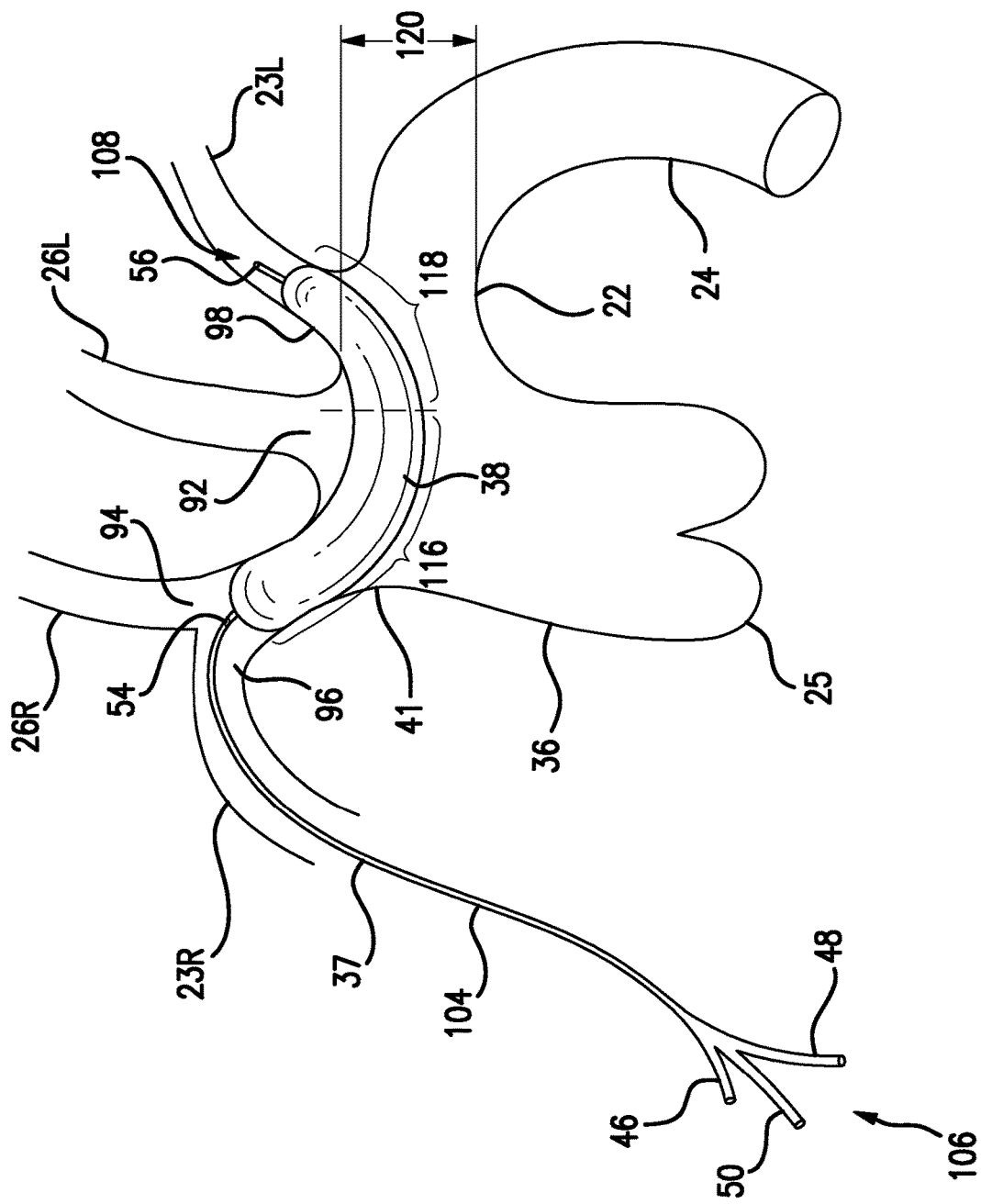
FIG. 14 is a front view of the patient with the occluding catheter of FIG. 13 in an inflated state.

Another exemplary embodiment of the occluding catheter 37 is shown in FIGS. 13 and 14. This embodiment achieves a temporary interruption of cerebral arterial inflow without placing the occluding catheter 37 into carotid arteries 26L and 26R by creating a single occluding balloon 38 extending the distance between the bifurcation of the innominate artery 41 and the orifice 98 of a left subclavian artery 23L. The single occluding balloon 38 may be provided so that no other occluding balloons, and in some instances no other balloons at all, are present on the occluding catheter 37.

When inflated, the occluding balloon 38 will effectively occlude the orifice of the right subclavian artery 96, the orifice of the right carotid artery 94, the orifice of the left carotid artery 92, and the orifice of the left subclavian artery 98 which are all branches of the aortic arch 22. This inflation will block flow into the brain by blocking flow through the right and left carotid arteries 26R and 26L and through both the right subclavian and left subclavian arteries 23R and 23L and, therefore, both right and left vertebral arteries. The occluding catheter 37 in this arrangement achieves complete avoidance of any manipulations on the carotid arteries 26R and 26L, thus eliminating the risk of induced injury or emboli 28, leading to stroke, problems that are known to occur in the prior art devices. As shown, the occluding balloon 38 is not located within the right or left carotid arteries 26R, 26L when inflated. The occluding balloon 38 may also not be located within the right subclavian artery 23R when inflated in some embodiments.

The occluding catheter 37 may be inserted via the peripheral artery of the right or left arm. FIGS. 13 and 14 show introduction through the right arm for vascular access. A guide wire 100 may first be passed via the brachial artery and advanced first into the innominate artery 41, then the aortic arch 22, and finally into the left subclavian artery 23L. The occluding catheter 37 will be next advanced over the guide wire 100 and consequently first into the innominate artery 41, then the aortic arch 22 and finally into the left subclavian artery 23L. The occluding balloon 38 extends from the level of the innominate artery 41 to the level of the left subclavian artery 23L.

Figure 15:
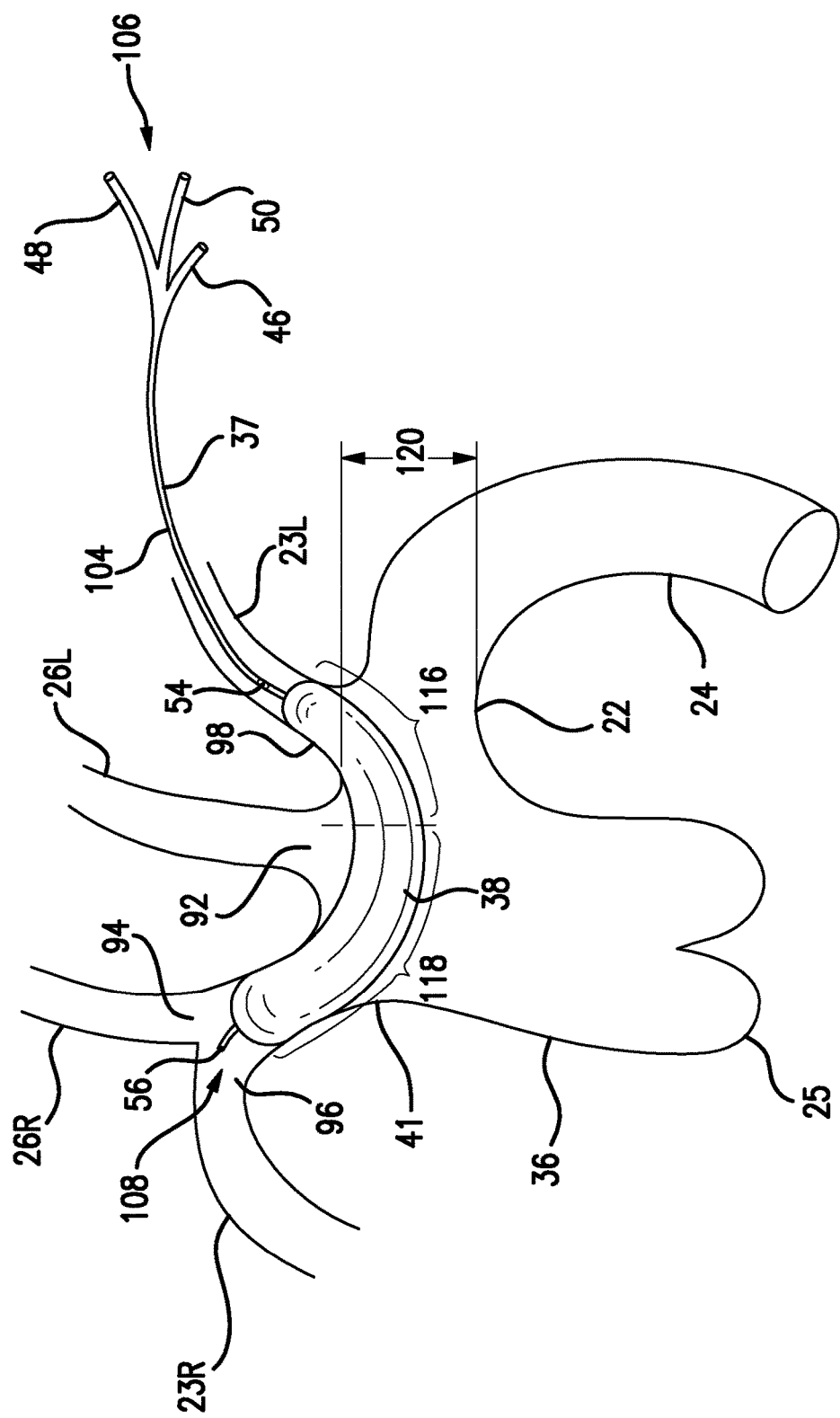
FIG. 15 is a front view of the patient with the occluding catheter of FIG. 13 in an inflated state but introduced instead through a left subclavian artery in accordance with a still further exemplary embodiment.

The left arm is used for insertion as shown in FIG. 15. The occluding catheter 37 is first advanced into the left subclavian artery 23L, then the aortic arch 22, and then into the innominate artery 41 and right subclavian 23R artery. The occluding balloon 38 extends through the whole distance between the left and right subclavian arteries 23L, 23R. Inflation of the occluding balloon 38 occludes the orifices 96, 94, 92, and 98 to completely prevent the emboli 28 from entering cerebral circulation via all potential ways of arterial inflow. Pressure in the right subclavian artery 23R may be measured using the distal tip opening 56, and opening of the shaft 54 can be used to measure blood pressure in the left subclavian artery 23L.

Although the occluding balloon 38 is a single occluding balloon introduced through the left arm of the patient in FIG. 15, should the occluding catheter 37 include proximal and distal occluding balloons 38, 42 and be desired for insertion through the left arm the relative occluding balloon 38, 42 sizes may be varied. For example, the distal occluding balloon 42 may be larger in diameter 112 than the diameter 110 of the proximal occluding balloon 38. The distal occluding balloon 42 when inflated may block flow through the innominate artery 41, and the proximal occluding balloon 38 would block flow through the left carotid artery 26L. The segment 44 would be between the balloons 38, 42 and would be located in the aortic arch 22. The proximal portion of the occluding catheter 37 may be located within the left subclavian artery 23L. Placement may be effected by first inflating the distal occluding balloon 42 to allow arterial blood flow to naturally pull it into the innominate artery 41. The distal occluding balloon 42 may be deflated to allow for determination of the positioning of the occluding catheter 37. The proximal occluding balloon 38 may be inflated to determine its positioning as it may block flow through both the left carotid artery 26L and the left subclavian artery 23L.

Although described as blocking flow through both of the carotid arteries 26R and 26L, it is to be understood that only one of the carotid arteries 26R or 26L may be blocked in certain arrangements and uses of the occluding catheter 37.

The size and shape of the occluding balloon 28 can vary depending on the patient's anatomy and the size of the arteries discussed herein. For this purpose it may be the case that low pressure, highly compliant occluding balloons 38 of conical and ovoid shape are used with larger central segments corresponding to the patient's innominate artery 41, and aortic arch 22, and the narrower peripheral segments corresponding to the level of right and left subclavian arteries 23R and 23L. The large segment of the occluding balloon 38 should be large enough to occlude the innominate artery 41 and the orifice 92 of the left carotid artery 23L, but not too large to compromise the lumen of the aortic arch 22. It may be made sufficiently compliant to assure slight herniation into the orifices 96, 94, 92 and 98 during inflation. Thus in some arrangements, the occluding balloon 38 may extend into any one of or all of the arteries 23R, 26R, 26L and 23L.

The diameter 120 of the aortic arch 22 is larger than the diameter 110 of the occluding balloon 38 when the occluding balloon 38 is inside of aortic arch 22 and is inflated. This arrangement will block blood flow through the carotid arteries 26R, 26L but will allow for divergence of blood flow carrying the emboli 28 into the distal aorta 24 and away from the cerebral circulation. The maximal diameter 110 of this segment of the occluding balloon 38 within the aortic arch 22 may not exceed 60-70% of the diameter 120 of the aortic arch 22. In other arrangements, the diameter 110 within the aortic arch 22 may be up to 25%, up to 35%, 50%, or up to 60% of the diameter 120.

Although described as preventing emboli 28 from flowing through the carotid arteries 26R, 26L, the occluding catheter 37 may also be used to prevent emboli 28 from flowing through the right subclavian artery 23R and/or the left subclavian artery 23L. This prevention may be in addition to or alternatively to prevention of flow through the carotid arteries 26R and/or 26L.

The occluding catheter 37 may be wireless in that it can be placed within the patient without the use of a guide wire 100. When provided with a pair of occluding balloons 38 and 42, the distal occluding balloon 42 may be referred to as a "floating" balloon to allow for wireless catherization of the aortic arch 22 branches. The distal occluding balloon 42 may be fully or partially inflated and through the size of the fully or partially distal occluding balloon 42 will be propelled into one of the branches 23L, 26L, 41 of the aortic arch 22 while the occluding catheter 37 is gently advanced or pulled back (manipulated) until it reaches the target artery. The desired location of the distal occluding balloon 42 may be the left carotid artery 26L or left subclavian artery 23L if the occluding catheter 37 is inserted via the right arm of the patient. The desired location of the distal occluding balloon 42 may be the right subclavian artery 23R, the innominate artery 41, or the right carotid artery 26R if the occluding balloon 42 is inserted via the left arm of the patient. In other arrangements, when a single occluding balloon 38 is used instead of a distal occluding balloon 42 and a proximal occluding balloon 38, the single occluding balloon 38 may also be drawn into one of the aforementioned branches of the aortic arch 22 via natural blood flow pulling and be a wireless placement.

The occluding balloon 38, or the proximal occluding balloon 38 and distal occluding balloon 42 when two are present, and the shaft 104 are arranged so that when inflated all of the blood into the artery in question (23L, 26L, 26R, 23R and/or 41) is blocked. In this regard, no blood flows past the inflated balloon 38 or 38, 42 or the shaft 104. Blood does not flow through any channel or any portion of the shaft 104 into any of the arteries 23L, 26L, 26R, 23R and/or 41. The arteries 23L, 26L, 26R, 23R and/or 41 may be completely prevented from having blood flowing through them as per the arrangement of all portions of the occluding catheter 37. The segment 44 may be arranged so that access to an inner channel of the shaft 104 is not possible. In this regard, the segment 44 may be solid and capable of blocking blood flow such that no blood enters segment 44 when the occluding balloons 38 and 42 are inflated and are located in the patient. The shaft 104 is arranged so that blood does not flow from the aortic arch 22 into the shaft when the occluding catheter 37 is oriented in the patient and used to reduce emboli 28 through the carotid arteries 26R, 26L.

In other arrangements, the occluding balloon 38, or proximal occluding balloon 38 and distal occluding balloon 42 when two are present, and the shaft 104 are arranged so that some blood does flow into arteries 23L, 26L, 26R, 23R and/or 41. The balloon 38 or 38, 42 can be partially inflated but not inflated all the way to seal the arterial wall. The balloon 38 or 38, 42 can be made so that even if fully inflated it is small enough not to completely block blood flow to seal the arterial wall. Some amount of blood can in fact flow past the inflated balloon 38 or 38, 42 and into the various arteries 23L, 26L, 26R, 23R and/or 41. The blood that flows past is unfiltered blood. Although emboli 28 may still flow into cerebral circulation and cause stroke, even partial reduction of flow will cause a partial reduction in the chance of stroke or the severity of stroke. The occluding catheter 37 may block from 30%-50%, from 50%-70%, from 70%-90% or up to 100% of the blood flow into the various arteries 23L, 26L, 26R, 23R and/or 41 in accordance with certain exemplary embodiments. Blood that does flow into the various arteries 23L, 26L, 26R, 23R and/or 41 comes directly from the aortic arch 22 and is unfiltered. As used herein, the term "occlude" is broad enough to include complete blockage of blood flow and to include partial blockage of blood flow while still allowing some unfiltered blood to flow through. Also, as used herein when referring to a "block" of blood flow, it is to be understood that this term is broad enough to cover complete blocking of blood flow and partial blocking of blood flow such that some amount of unfiltered blood flows through.

In use, the occluding catheter 37 may be used so that partial inflation or total inflation of the occluding balloons 38 or 38, 42 is made during a medical procedure to control the blood flow through by reducing the risk of stroke while still allowing blood to enter the cerebral circulation. When fully inflated to completely block blood flow, the occluding balloons 38 or 38, 42 are solid components and not filters and do not filter emboli 28 but rather prevent everything including blood and emboli 28 from moving therethrough. The occluding balloons 38 or 38, 42 and tube sections of the occluding catheter 37 may completely block blood and emboli 28 from moving through the particular blood vessel such that no blood or emboli 28 flows through the tube sections of the occluding catheter 37 past the occluding balloons 38 or 38, 42. The occluding balloons 38 or 38, 42 and the tubular sections of the occluding catheter 37 located at the blocked area of blood/emboli 28 flow when positioned are not porous members and do not filter any blood. However, when the occluding balloons 38 or 38, 42 are deflated, partially deflated, or fully inflated but less than the diameter of the vessel they are in allow blood and emboli 28 to flow around them through the particular blood vessel and they are not filtered in any manner, although the flow rate may be decreased due to the presence of the occluding balloons 38 or 38, 42 and tubular sections of the occluding catheter 37.

Information Added in Continuation-in-Part Application

The odds of embolic particles 28 and 30 breaking loose and migrating into cerebral vessels 26R, 26L are minimal when the heart 21 is relaxed and/or not ejecting blood. This is observed in patients on cardiopulmonary bypass when the heart 21 is not filled with blood and is unable to eject or is in diastolic arrest. Diastolic arrest is a condition when the heart 21 is not contracting while being totally relaxed (diastole). Echocardiography in this situation will frequently show particles of air that are enclosed in the heart chambers. When the heart 21 is filled with blood and starts contracting, these particles 28 and 30 start moving and ultimately get ejected into the aortic arch 22 and its branches leading to cerebral emboli and stroke. Transcranial Doppler evaluation of middle cerebral arteries at this stage of the procedure may detect an appearance of high intensity microembolic signals (HITS) that confirm the process of embolization of cerebral arteries occurring with each cardiac contraction and ejection of blood into the aorta 22.

These particles 28, 30 may stay trapped inside the heart 21, pulmonary veins, and aorta 22 for a significant amount of time even after resumption of cardiac ejection. The embolic events may occurs minutes or even hours after "emboligenic" intervention. Each cardiac contraction and ejection of blood from the left ventricle in this setting will be associated with the release of multiple embolic substances 28, 30 from the heart 21, aortic valve 25 and ascending aorta into systemic circulation and the carotid arteries 26R, 26L, leading to embolic stroke.

A system 200 may be provided to temporarily block or decrease blood flow to the carotid arteries 26R, 26L and the brain at the moment of cardiac contraction (systole) when the risk of embolization is maximal, but to allow for reconstitution of the carotid blood flow when heart 21 relaxes (diastole). This approach may decrease the amount of particles 27 reaching the brain with each systolic ejection of the heart 21 by virtue of their divergence away from the brain into the more distal branches of the aorta 24. Additionally, this approach may provide an adequate blood flow to the brain during cardiac diastole—the phase of cardiac contraction know to be essential for optimal cerebral blood flow. The fact that the duration of cardiac diastole is significantly longer that the duration of systole allows assuring adequate blood supply to the brain in spite of brief "systolic" interruptions of cerebral arterial inflow.

The occluding catheter 37 may be employed in the system 200 that monitors a cardiac cycle of a heart 21 of a patient and synchronizes the occluding catheter 37 with the cardiac cycle so that the occluding device 37 blocks blood flow during some phases of the cardiac cycle and allows more blood flow during other phases of the cardiac cycle. The provided apparatus and method prevents stroke by diverting emboli 28, 30 from cerebral circulation while providing adequate flow to the brain. The occluding catheter 37 can be introduced into the aortic arch 22 in any manner previously discussed and may include proximal and distal occluding balloons 38 and 42, or may have a single occluding balloon 38. The occluding catheter 37 can be arranged in any manner as previously discussed when used in the system 200. The occluding ballon(s) 38, 42 may be inflated to provide blocking of blood flow to the carotid arteries 26 R, 26L during a systole phase of the cardiac cycle to prevent blood flow and emboli 28, 30 from entering the brain and causing stroke. In order to assure adequate blood flow to the brain through the carotid arteries 26R, 26L, the balloon(s) 38, 42 may be deflated during the diastole phase, and if needed in some arrangements early systole, when the heart is relaxed or not yet ejecting and the risk of ejection of emboli 30 into the aorta 22 and carotid arteries 26R, 26L is minimal.

Figure 16:
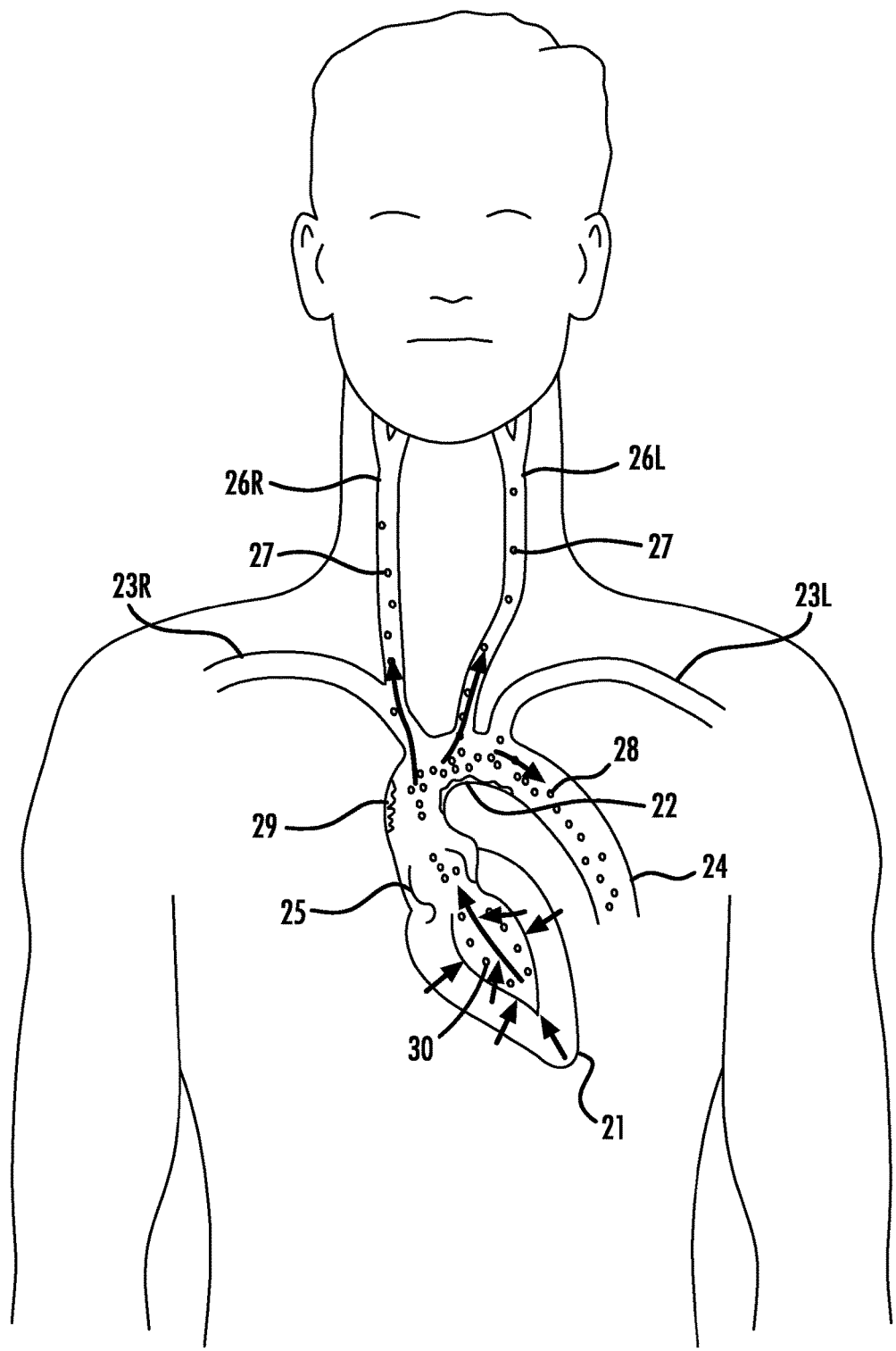
FIG. 16 is a front view of a patient with a heart in a systole phase.

With reference again to FIG. 1, emboli 27, 28 and 30 may be present in the circulatory system through the previously listed conditions and procedures which may find their way through the carotid arteries 26R, 26L and into cerebral circulation. The intracardiac emboli 30 may include air, gas, thrombi and atherosclerotic materials. FIG. 16 shows the heart 21 in a systole phase of the cardiac cycle in which the heart 21 contracts/squeezes and blood is pumped therefrom. The contractions of the heart 21 (systole) will lead to opening of the aortic valve 25 and ejection and washout of emboli 30 into the aorta 22 with the most direct anatomical target being the carotid arteries 26R, 26L and the brain. Emboli 27 will thus be pushed into and through the carotid arteries 26R, 26L when the heart 21 contracts in the systole phase of the cardiac cycle. This may be the time of the cardiac cycle when a timely interruption or mere reduction of flow through the carotid and subclavian, and therefore vertebral, arteries will decrease the risk of entry of emboli 27 into the cerebral circulation and will prevent or significantly diminish the risk of stroke.

Figure 17:
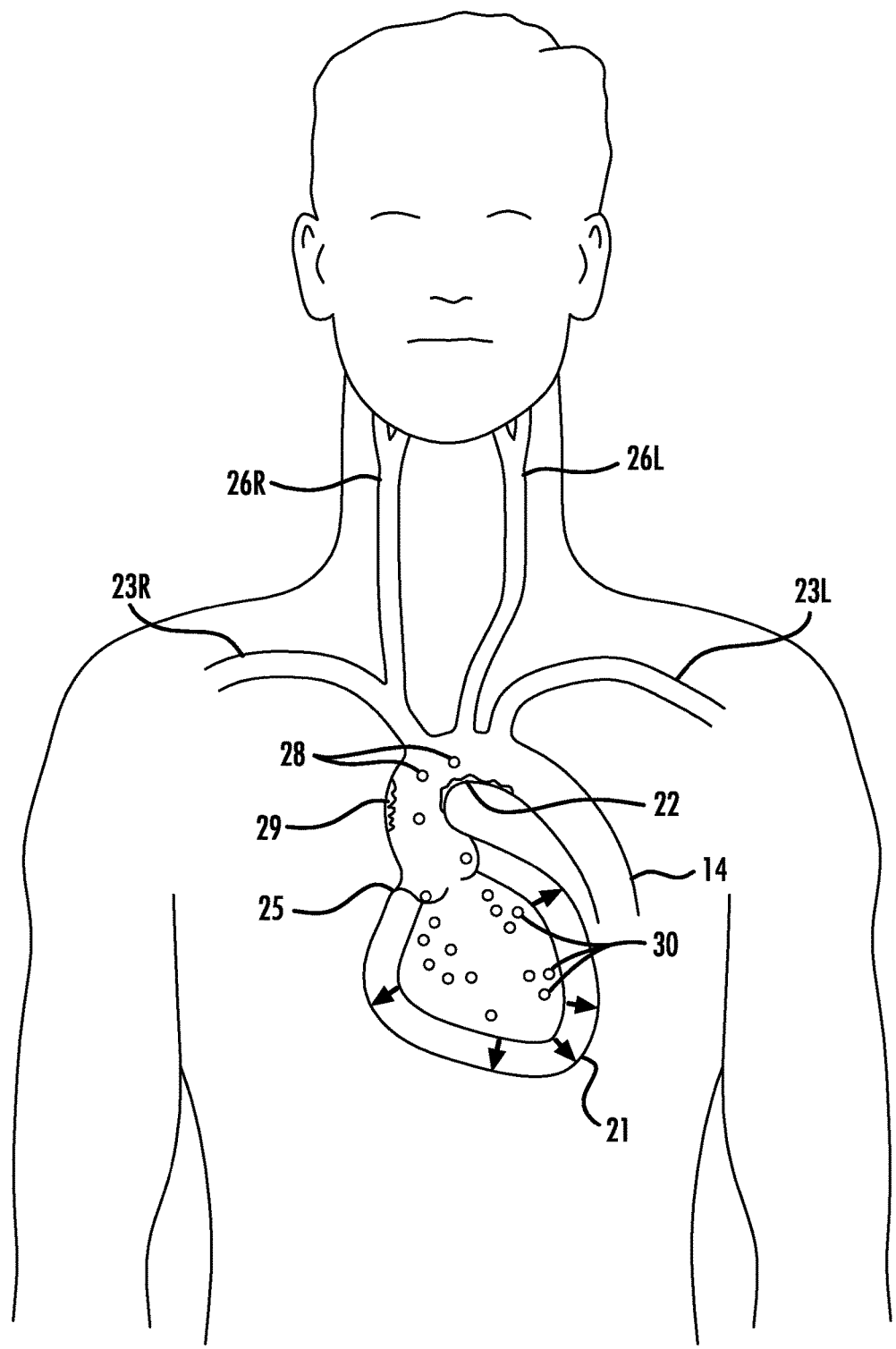
FIG. 17 is a front view of a patient with the heart in a diastole phase.

FIG. 17 shows the heart 21 in a diastole phase of the cardiac cycle in which the heart 21 muscles relax and blood fills the chambers of the heart 21. As shown, the heart 21 expands from the systole phase during cardiac relaxation and blood ejection is significantly decreased or even totally absent along with washout of intra-cardiac particles 30 from the heart 21 and aorta 22. At this phase of the cardiac cycle, that is diastole and potentially even early systole, the flow to the brain does not have to be interrupted and the temporary occlusion of cerebral vessels may be relieved, thus providing blood flow to the brain and avoiding ischemia.

Figure 18:
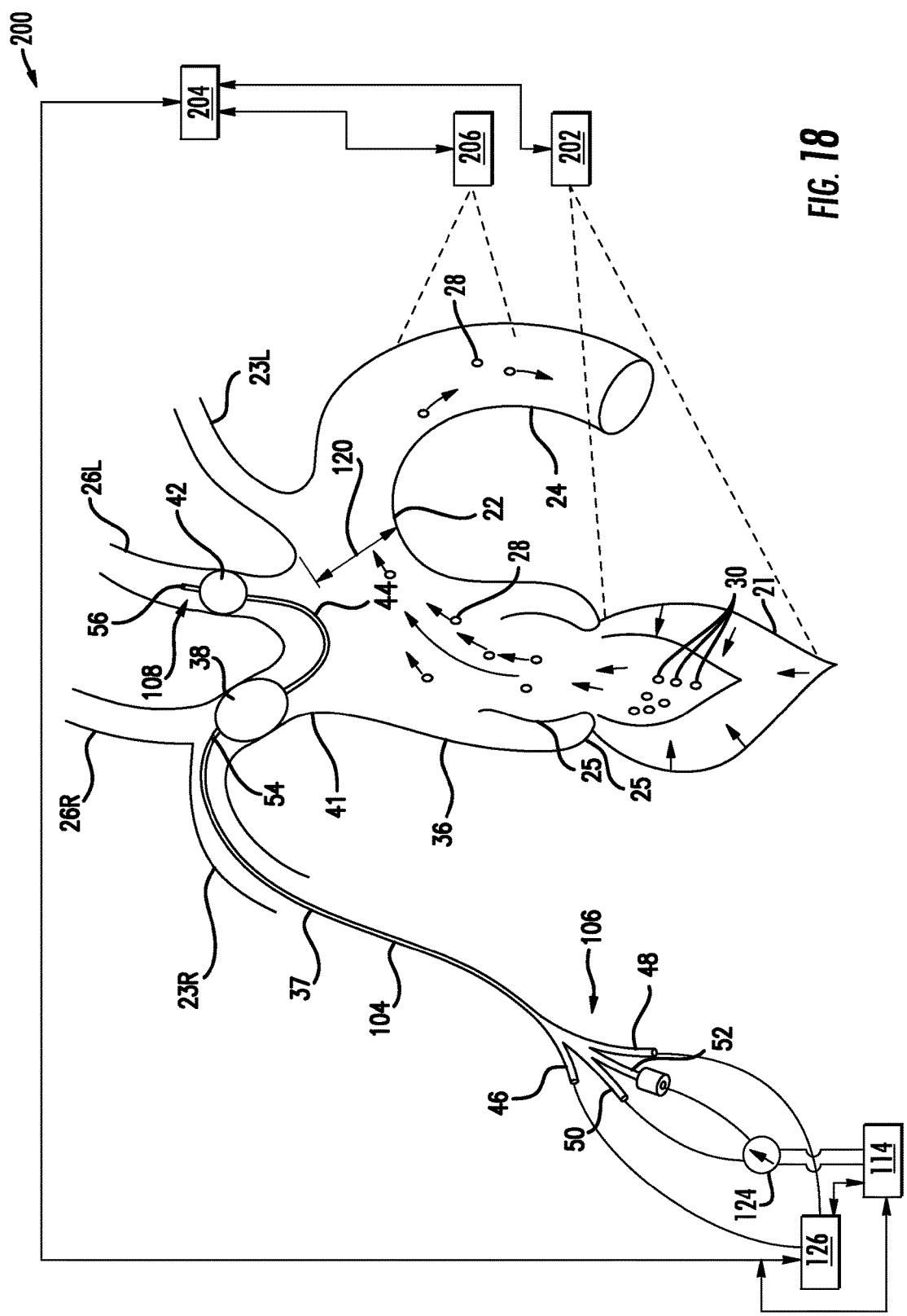
FIG. 18 is a front view of a system with a catheter having two balloons expanded when the heart is in a systole phase.
Figure 19:
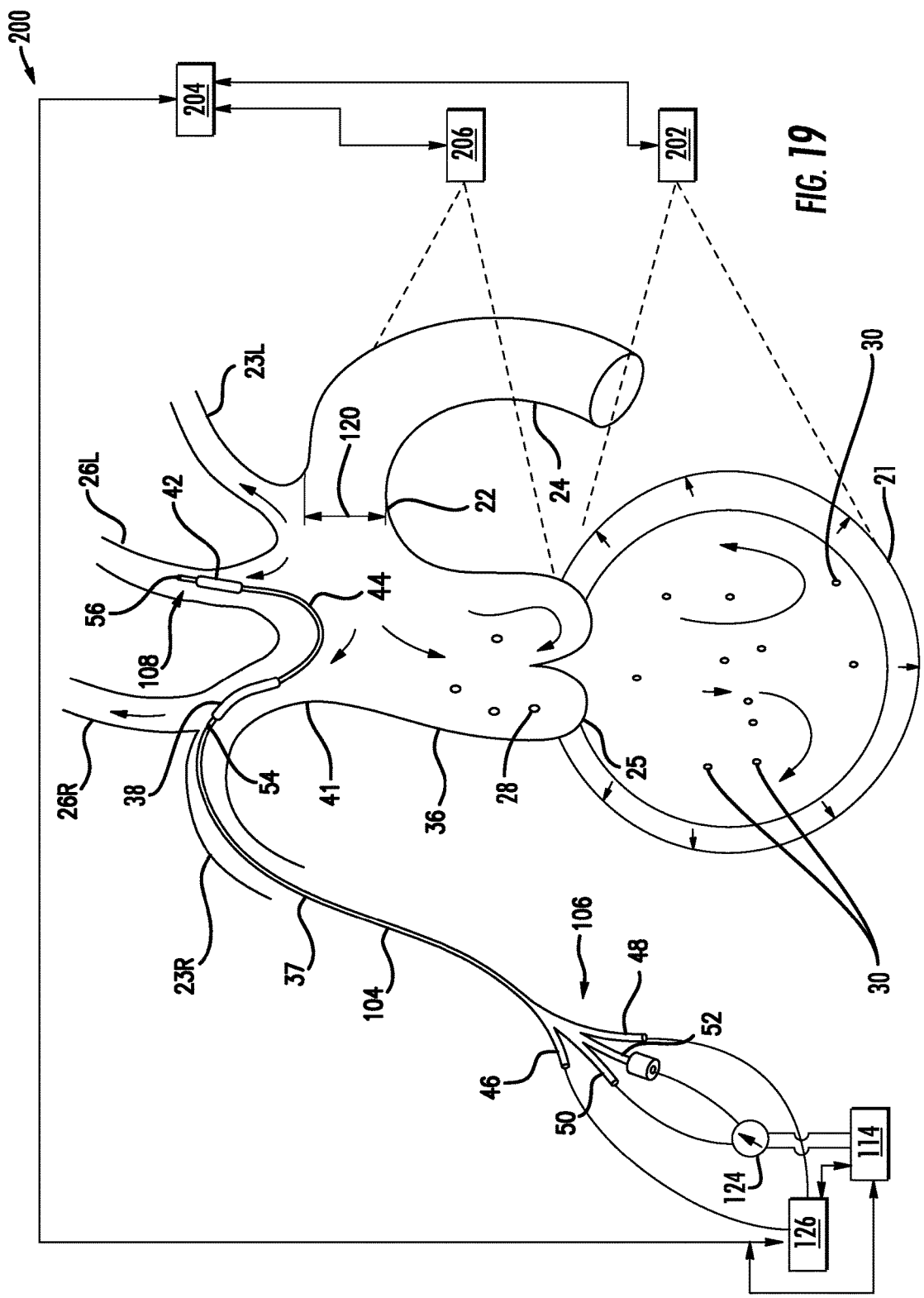
FIG. 19 is a front view of the system of FIG. 18 with the heart in a diastole phase and the balloons unexpanded.

FIGS. 18 and 19 show an exemplary embodiment of the disclosed method of diverging emboli 27, 28, 30 from cerebral circulation by exerting cyclical recurring internal occlusion (partial or complete) of the arteries 26R, 26L, 41, 23R and 23L. Blood flow may be limited in that it is completely prevented from moving through the carotid arteries 26R, 26L, and in some instances the subclavian arteries 23R, 23L, or so that the blood is partially limited in moving through the carotid arteries 26R, 26L such that some blood flows through the carotid arteries 26R, 26L but not as much as would be the case through normal circulation if no occluding catheter 37 were present. The arrows show the deflection of the blood flow, containing emboli 28, into the descending aorta 24.

The inflation of balloons 38 and 42 leads to a temporary pressure gradient and the interruption of carotid flow during cardiac systole and ejection. This expansion/inflation may be synchronized with the phases of the heart cycle in such a way that blood flow through the innominate artery 41 and the left carotid artery 26L is blocked during cardiac systole, or the part of systole when the heart 21 ejects. The inflation of the balloons 38, 42 is also synchronized in which it is partially or completely released during diastole. The actuation of the occluding catheter 37 may be triggered through monitoring the cardiac cycle by a cardiac monitoring device 202 such as EKG machines, arterial pressure waveform devices, or pulse oximetry devices. In this regard, the expansion of the occluding members 38, 42 may be triggered by the "R" wave of EKG, by the upstroke of the arterial blood pressure waveform, or by the upstroke of the pulse oximetry waveform.

Inflation of the balloons 38, 42 cause the emboli 28 to be diverted from the carotid arteries 26R, 26L and into the descending aorta 24 as previously discussed. Release of inflation pressure or otherwise contraction of the balloons 38, 42 is shown in FIG. 19. The release of pressure in the balloons 38, 42 during cardiac relaxation is not associated with ejection of emboli 30 from the heart 21 and embolization of the carotid arteries 26R, 26L. The aortic valve 25 is closed. It may be the case that there is a small amount of floating particles 28 in the ascending aorta 22. However, the chance of migration into the carotid arteries 26R, 26L in the absence of cardiac ejection, that is when the aortic valve 25 is open and blood is being pumped from the heart 21, is minimal. The deflation of the occluding members 38, 42 may lead to reestablishment of the carotid blood flow through the carotid arteries 26R, 26L and may assure adequate cerebral perfusion at the phase of the cardiac cycle when the risk of cerebral emboli 27 and stroke is minimal. There may be a small amount of floating particles 28 in the ascending aorta 22, however their chance of migrating into the carotid arteries 26R, 26L in the absence of cardiac ejection is small.

The entire process of inflating the balloons 38, 42 and releasing pressure to deflate the balloons 38, 42 can be repeated (cycled) in concert with the cycles of systolic contraction and diastolic relaxation in the cardiac cycle. The cycling process can be started before the surgical procedure or at some point during the surgical procedure that is likely to form emboli 28, 30. Also, the circulatory system can be monitored and once the presence of emboli 28, 30 is detected the inflation/deflation cycle can be started.

The members 38 and 42 can be expanded from an unactuated state to an actuated state depending on the phase of cardiac cycle in which the members 38 and 42 create an obstruction of the arteries 41, 26 and 23 to decrease the inflow of blood and hence the flow of potential emboli 27 into to cerebral circulation. Emboli 27, 28, 30 that are formed in the heart secondary to emboligenic intervention and are ejected into the aorta 22 during the ejection phase of the cardiac cycle are diverted from carotid arteries 26R, 26L into descending aorta 24. On the other hand, in order to assure adequate blood flow to the brain and to prevent its ischemic injury the occlusion of flow to carotid arteries 26R, 26L is interrupted during diastole and if needed early systole when the heart 21 is relaxed or not yet ejecting and the risk of ejection of emboli 30 into aorta 22 and carotid arteries 26R, 26L is minimal.

FIG. 18 shows a system 200 that may be used to execute the inflation/deflation cycle. The system 200 may include an occluding device 37 that can be arranged or provided in any manner as previously discussed. An actuation device 126, that in this embodiment is a pressure supply 126, is present and is in communication with the inflation ports 46 and 48 in order to cause inflation and deflation of the balloons 38 and 42. The actuation device 126 may cause the occluding catheter 37 to move from an actuated state to an unactuated state, and in some arrangements may cause the occluding catheter 37 to move to a partially actuated state in which the balloons 38, 42 are inflated to some amount between the actuated and unactuated states. The actuation device 126 may be a pressure source 126 in some exemplary embodiments that applies pressure when actuated, and then releases the pressure via a pressure release valve to unactuated/deflate the balloons 38, 42. In other arrangements, the actuation device may be a syringe or diaphragm that moves back and forth to push fluid into the balloons 38, 42 to inflate them and to pull fluid from the balloons 38, 42 to deflate them. The actuation device 126 may be any device capable of inflating and/or deflating the balloons of the occluding catheter 37.

The actuation device 126 may supply fluid, such as air, to the balloons 38, 42 in order to inflate them, and may withdrawal the fluid when the blockage of blood flow through the carotid arteries 26R, 26L is no longer desired. Here, the actuation device 126 may withdraw air from the balloons 38, 42 or a valve on the actuation device 126 may be opened for deflation. The actuation device 126 may be separate from the occluding catheter 37 or may have one or more components attached to and may be part of the occluding catheter 37.

The manometer 124 is shown in communication with ports 50 and 52 to read their pressures and to communicate same to the alarm system 114. Other manometers may be connected to the ports of channels 68 and 72 in order to control the degree of intravascular pressure created by the balloons 38, 42. The pressures read by the various manometers 124 may be sent to any of the components of the system 200.

The system 200 may include a cardiac monitoring device 202 that monitors the cardiac cycle of the heart 21. The cardiac monitoring device 202 can be an electrocardiogram (EKG) machine, a blood pressure waveform device, an arterial pressure waveform device, a cardiac pacing device, a pulse oximetry device or another mechanism to ascertain when the heart 21 is in a systole phase and a diastole phase. In other arrangements the cardiac monitoring device 202 may be carotid Doppler, trans-cranial Doppler, pulsation of the temporal arteries, Dopplerography, oscillotonometry, oximetry and other techniques of assessment of the carotid and cerebral perfusion. The cardiac monitoring device 202 may monitor the heart 21 or any portion of the circulatory system or other portion of the patient's anatomy in order to ascertain data relevant to the cardiac cycle.

The cardiac monitoring device 202 may be in communication with a synchronization device 204. Data may be transferred from the cardiac monitoring device 202 to the synchronization device 204, and in some arrangements data from the synchronization device 204 may be transferred to the cardiac monitoring device 202. The synchronization device 204 may be in communication with the actuation device 126 such that data from the synchronization device 204 is communicated to the actuation device 126. Likewise, the actuation device 126 may in turn communicate back to the synchronization device 204 in some arrangements. The synchronization device 204 may obtain data from the cardiac monitoring device 202 relevant to the phases of the cardiac cycle the heart 21 is experiencing. Using this data, the synchronization device 204 may match the creation and removal of the inflation and deflation to match the desired phases of the cardiac cycle. The synchronization device 204 may deliver a command to the actuation device 126 to cause the actuation device 126 to inflate balloons 38, 42 when desired. Likewise, the synchronization device 204 may deliver a command to the actuation device 126 to cause the actuation device 126 to not actuate the occluding catheter 37.

The synchronization device 204 may be a computer that has a processor and a memory in some exemplary embodiments. The synchronization device 204 may be a part of the cardiac monitoring device 202, actuation device 126 and/or occluding catheter 37 in accordance with various exemplary embodiments. The synchronization device 204 may simply be a portion of one of these components 202, 37 and/or 126 that syncs the formation and removal of the pressure with the cardiac cycle as desired. The synchronization of the application and removal of pressure causes the blood flow through the carotid arteries 26R, 26L to be dynamically blocked which leads to transient interruption of carotid blood flow. Although a single cardiac monitoring device 202, synchronization device 204, and actuation device 126 are shown any number of these devices may be present in system 200 in other exemplary embodiments.

The degree of the residual pressure in the balloons 38, 42 during cardiac relaxation may vary depending on the adequacy of the diastolic cerebral blood flow. The divergence of cerebral emboli 27 and prevention of stroke throughout multiple cardiac cycles and for an extended period of time can be achieved through this method that involves blockage of blood flow through the carotid arteries 26R, 26L at the time of cardiac systole and unblocking during diastole. For short periods of time (that may be longer in patients under hypothermia) both systolic and diastolic restriction of the carotid flow can be achieved. As such, the blockages of the carotid arteries 26R, 26L may be formed during all phases of the cardiac cycle for any length of time as may be desired. In these instances, there is not a dynamic cycling of the blockage of flow through the carotid arteries 26R, 26L, but rather a static continuous blockage of the carotid arteries 26R, 26L.

The extent and timing of actuation of the occluding catheter 37 can vary depending on the variations of cardiac pathology and physiology. The system 200 may be arranged with an option to delay, accelerate, prolong or shorten the length and intensity of the blockage with the resulting goal of minimizing the degree of cerebral embolization while assuring adequate cerebral perfusion with the minimal trauma to the underlying structures onto which forces are applied. Although described as being pulsated in a dynamic fashion based upon the cardiac cycle, or in a static fashion irrespective of the cardiac cycle, the system 200 can be arranged so that both of these methods are employed. For example, certain ones of the balloons 38, 42 may be pressurized to cause consistent static blocking of one of the carotid arteries 26R or 26L while the other balloon 38, 42 may be dynamically pulsated in sync with the carotid cycle. In some embodiments, one of the carotid arteries 26R/26L can be statically blocked, and the other carotid artery 26R/26L can be cyclically blocked. The ability to use both static and dynamic, cyclical blocking may allow achievement of optimal individual regime of alteration of the cerebral blood flow.

The system 200 may also include an emboli monitoring device 206 that can monitor the heart 21, aortic arch 22, carotid arteries 26R, 26L or any other portion of the circulatory system for the presence of emboli 27, 28, 30. The emboli monitoring device 206 is shown in communication with the synchronization device 204, but may be in direct communication with the actuation device 126 or any other portion of the system 200 in other arrangements. The emboli monitoring device 206 upon detection of the appearance of potential emboli 27, 28, 30 in the heart cavities or other portions of the circulatory system may send this information to the synchronization device 204 (or other component to which it is in communication) which then causes the balloons 38, 42 to actuate via the actuation device 126. The initiation of the inflation may be continued in a cyclical nature as previously discussed, or may be static in nature in that the inflation is applied through all phases of the cardiac cycle. The emboli monitoring device 206 may be transcranial Doppler ultrasound, carotid Doppler study, and/or transesophageal echocardiography. Further, the emboli monitoring device 206 may be the same type of device or method as disclosed herein with respect to the cardiac monitoring device 202. In certain exemplary embodiments, the emboli monitoring device 206 and the cardiac monitoring device 202 are the same device and are not separate devices.

Although described as automatically starting the actuation of occluding catheter 37 and blocking of the carotid arteries 26R, 26L when emboli 27, 28, 30 are discovered by the emboli monitoring device 206, it may be the case that instead of automatically starting actuation of the occluding catheter 37 the health care professional is given the option of manually starting the inflation. An alarm can be triggered through sensing of the emboli monitoring device 206 and the health care professional may decide to begin the inflation if desired.

Figure 20:
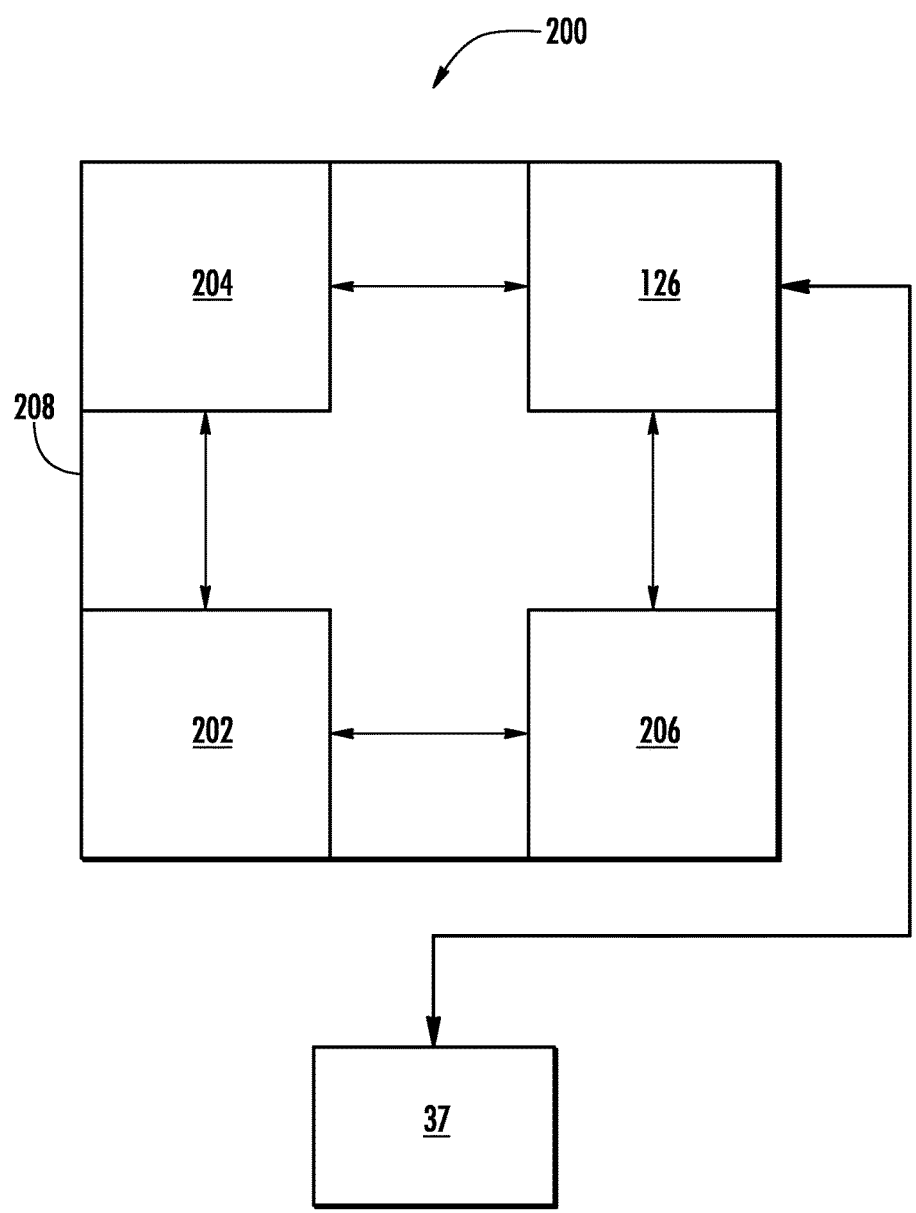
FIG. 20 is a schematic view of an alternative arrangement of the system in which the various devices are integrated into a single device.

The system 200 can be arranged so that all of the functions of the cardiac monitoring device 202, synchronization device 204, emboli monitoring device 206, and actuation device 126 are performed by a single device 208 as shown for example in FIG. 20. Here, a processor and a memory may be included in the single device and the various functions of the aforementioned devices 204, 126, 202, 206 can be executed by the processor, memory, sensors, and pump of the single device 208. In other arrangements, one or more of the various devices 204, 126, 202, 206 can be separate from the single disclosed device 208 but in communication therewith. The occluding catheter 37 may be actuated and released through communication with the single device 208. The occluding catheter 37 may be attached to the actuation device 126 portion of the single device 208.

A method for reducing or eliminating stroke during a surgical procedure may first involve a brief actuation of the balloons 38, 42 to ensure adequate placement of the occluding catheter 37. This can be confirmed by carotid Doppler, a pressure gauge, percutaneous oximetry, transcranial Doppler, or other method. This compression process is synchronized with the cardiac cycle by means of EKG, pressure waveform, pacing, oximetry, Dopplerography, echocardiography or other ways of cardiovascular monitoring. The process implements the idea of increasing the blockage of blood flow to or through the carotid arteries 26R, 26L when the heart 21 is ejecting (systole) and decreasing it when the heart 21 is relaxing (diastole).

Once proper positioning is confirmed, the inflation force may be released and carotid blood flow can be confirmed if desired. The cardiac synchronization mode of function of the system 200 is initiated where the actuation of the occluding catheter 37 is triggered by the electrophysiological, mechanical, or other indices of the cardiac cycle. The systolic pressurization and diastolic relaxation of the occluding catheter 37 is then started for a period of time necessary for complete clearance of the heart 21, its structures and aorta 22 from all potential emboli (usually, between 45 and 360 cardiac cycles). The whole process can be repeated any time and on multiple occasions when the possibility of the residual or newly formed intra-cardiac or intra-aortic emboli 28 and 30 is anticipated. It is therefore the case that the occluding catheter 37 cycles to cause blockage within the circulatory system and to remove blocking within the circulatory system to block and unblock flow through/to the carotid arteries 26R, 26L a plurality of times over and over again. During the times that the carotid arteries 26R, 26L are not being blocked, generally during the diastole phase, blood flow may go through the carotid arteries 26R, 26L and into the brain. Blood flow may thus go to the brain with the risk of emboli 27 being transferred to the brain small or non existent.

Should the emboli monitoring device 206 (i.e. cardiac ECHO, vascular Doppler ultrasound, pulse oximetry, transcranial Doppler, echocardiography, arterial Doppler ultrasound, cerebral oximetry, or other) detect the presence of particulate material in the heart 21 chambers, ascending aorta 22 or cerebral arteries an alarm would go off with an option of automatic re-initiation of the process of synchronized carotid blocking. The inflation pressure would be released during diastole to avoid undue interruption of the cerebral flow. The alarm, deflation and, if needed, inflation could be overridden by the physician when clinically indicated. Moreover, the duration of inflation may extend through several cardiac cycles if indicated.

The timing of the blockage in relation to the phases of the cardiac cycle may vary from making the duration of blockage or unblocking of the expandable components of the occluding catheter 37 equal to, shorter or longer than the duration of systole and diastole. In some arrangements, the blockage may be applied at all times during the systole phase, and removed at all times during the diastole phase. The systole phase may be broken up into an early portion and a remaining portion. In the early portion of the systole phase the heart 21 may not yet be ejecting blood or emboli 30. Here, the chance of directing emboli 27 through the carotid arteries 26R, 26L is minimal. Blockage through inflation of the balloons 38, 42 may not be applied during the diastole phase and the early systole phase, but may be applied during the remaining portion of the systole phase.

The blocking force may be strong enough to completely prevent blood flow through the carotid arteries 26R, 26L, or may only partially prevent blood flow through the carotid arteries 26R, 26L. In some arrangements of the system 200, removal of the blocking force is complete removal such that there is no blockage at all of the carotid arteries 26R, 26L. In other embodiments, removal of the blocking is partial removal such that some compressive force remains on the carotid arteries 26R, 26L but not the full amount of the blocking force. In these arrangements, the carotid arteries 26R, 26L may be blocked some degree even when the inflation is removed. In general, the inflow of blood to cerebral arteries is decreased during cardiac ejection and is normalized or only partially decreased during cardiac relaxation.

The alarm system 114 may be included with the system 200 and can be a separate component or may be incorporated into one of the disclosed components of the system 200. The alarm system 114 may be in communication with one of the components of the system 200 or may not be in communication with any of the aforementioned components of system 200. The alarm system 114 may sound an alarm if the blockage of the carotid arteries 26R, 26L is performed for a certain amount of time, of if there is evidence of the detection of potential emboli 28, 30 via the emboli monitoring device 206.

The system 200 may also monitor the indices of the carotid and cerebral circulation during the blockage of the carotid arteries 26R, 26L and during the times in which the carotid arteries 26R, 26L are not compressed. This monitoring may be performed by one of the components or methods previously disclosed with respect to the devices 204, 126, 202, 206, or may be performed by a separate device or method.

The occluding catheter 37 may be positioned into the proper position within the circulatory system without the use of a guide wire 100. Another option is to position the occluding catheter 37 upstream from the carotid vessels 26R, 26L lessening significantly the mere contact with the carotid arterial wall, thus decreasing the risk of carotid trauma, emboli and stroke. The specific positioning and orientation of the proximal and distal occlusion balloons 38, 42 on the shaft 104 of the catheter 37 plays a role in a quick, effortless and safe placement of the occluding balloons 38, 42 leading to interruption of flow to carotid arteries 26R, 26L with only minimal or no contact with the carotid arterial wall.

The occluding catheter 37 can be configured in any manner previously discussed. The channel 70 is not in fluid communication with channels 68 and 72. However, the channels 68 and 72 can be in fluid communications with one another in those embodiments where a simultaneous inflation of both proximal and distal occluding balloons 38, 42 is desired. This arrangement would allow a single inflation channel for both occluding balloons 38, 42. Such single inflation channel can be larger to assure better responsiveness of the occluding balloons 38, 42 to variations of the intraluminal pressure. If channels 68 and 72 are not in fluid communication with one another, the proximal and distal occluding balloons 38, 42 may be inflated separately from one another such that one is inflated before another one, or such that both inflate simultaneously.

The distal occluding balloon 42 can be positioned in the left carotid artery 26L. However, if desired, its distal segment can be advanced into the left subclavian artery 23L, while its proximal segment can be left in the lumen of the aortic arch 22 while overlapping and blocking the orifice of the left carotid artery 23L at the same time. With the length of the distal balloon 42 exceeding 2-3 cm this arrangement will allow for simultaneous blockade of the blood flow to right carotid 26R, right subclavian 23R, left carotid 26L and left subclavian 23L arteries, thus protecting the whole area of cerebral perfusion from potential emboli.

At this moment interruption of the cerebral inflow for 1-2 minutes irrespective of the phase of cardiac cycle will protect the brain from the first event of the massive washout of the all potential debris from the heart 21 and aorta 22. Later, however, the initiation of the balloon 38, 42 inflation synchronously with cardiac contraction and ejection and its deflation during cardiac relaxation will provide further cerebral protection of potential emboli throughout the whole length of the procedure.

The method of dynamic occlusion has been described with reference to an occluding catheter 37 that has a proximal occluding balloon 38 and a distal occluding balloon 42 integrated into the system 200. However, all of the other arrangements of the occluding catheter 37 described herein could be used in the dynamic occlusion system 200. For example, the occluding catheter 37 as shown and described with reference to FIG. 12 can be incorporated into the system 200 and can have two or more proximal and distal chambers with an option of separate versus simultaneous expansion of these chambers. In this embodiment, the distal chamber may be inflated first in order to facilitate the passage of the distal portion of the balloon 42 into the left subclavian artery 23L or if desired into the left carotid artery 26L while propelled with the forward arterial flow. This arrangement may combine the potential of the first two embodiments, described above and may not require a guide wire 100 for its insertion thus decreasing the risk of an additional trauma to the vessel wall with a potential for a stroke. However, in order to facilitate the advancement of the occluding catheter 37 in patients with difficult anatomy, the device 37 may have an option of an extra lumen 50, 56, accommodating a guide wire 100, should wireless advancement of the catheter 37 into the left carotid 26L or left subclavian 23L artery prove to be difficult. This device 37 without guide wire 100 incorporation will achieve an avoidance of any manipulations on carotid arteries 26R, 26L and a possibility of a wireless insertion, with the much lower risk of the arterial wall injury, cerebral emboli and stroke-problems known to occur with prior devices. The balloons 38, 42 in the FIG. 12 embodiment can be inflated or expanded during systole and can be uninflated or contracted during diastole or even during the early portion of the systole phase to achieve dynamic occlusion as discussed.

Figure 21:
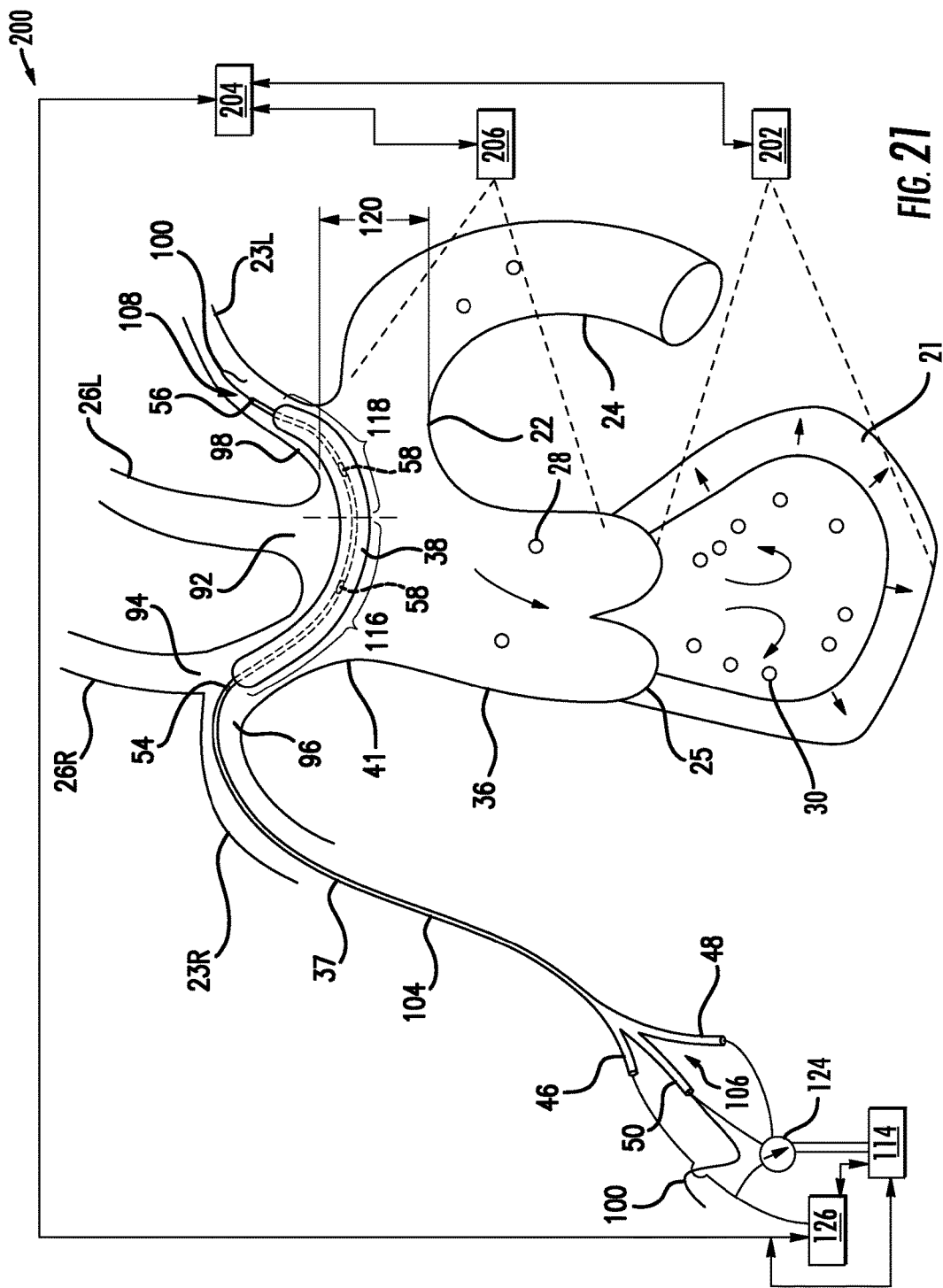
FIG. 21 is a front view of a system in another alternate embodiment having a catheter with one balloon with the heart in a diastole phase.
Figure 22:
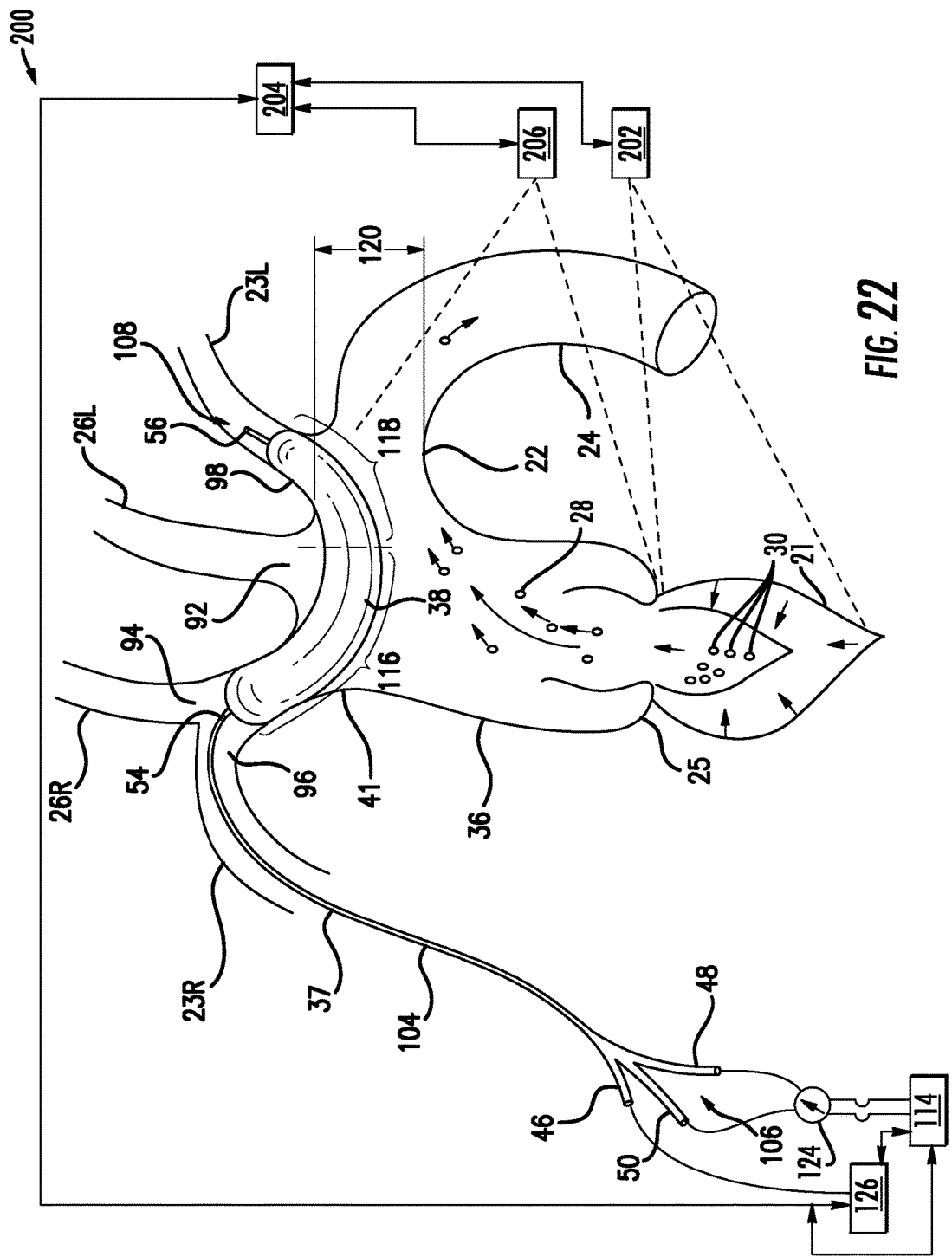
FIG. 22 is a front view of the system of FIG. 21 with the heart in a systole phase.

In some instances of difficult anatomy, however, the passage and positioning of said occluding catheter may require the use of the guide wire 100. FIG. 21 shows the system 200 with a guide wire 100 through the occluding catheter 37 to aid in placement. The occluding catheter 37 that is used is the one previously described with respect to FIG. 13. The heart 21 is in a diastole phase of the cardiac cycle and the occluding balloon 38 is relaxed and blood is allowed to flow through the various orifices 96, 94, 92, 98. The guide wire 100 may be removed once positioning is ascertained.

The occluding balloon 38 is expanded via the port 46, attached to the manometer 124 and the actuation device 126 as shown in FIG. 21. This expansion occurs when the cardiac monitoring device 202 detects the heart 21 in the systole phase. The actuation device 126 can inflate and release the occluding balloon 38 according to the phases of cardiac cycle. The expansion of the balloon occurs during the ejection phase of the heart 21, while the deflation occurs during diastole and early systole allowing for diastolic perfusion of the carotid 26R, 26L and subclavian 23R, 23L, and vertebral arteries.

The geometry and the method of insertion of the transaortic occluding balloon 38 (and 42 if present) will slightly differ depending on the site of its insertion. When the right arm is used for vascular access the balloon 38 will be inserted via the right radial or brachial artery and advanced first into innominate artery 41, then aortic arch 22, and finally into the left subclavian artery 23L with the body of the balloon 38 extending from the level of the innominate artery 41 to the level of the left subclavian artery 23L. When the left arm is used for balloon insertion, for example in the FIG. 15 embodiment, the catheter 37 may be inserted via the left radial or brachial arteries and advanced into the left subclavian artery 23L first, then aortic arch 22 and then innominate artery 41 and/or right subclavian 23R artery with the body of the balloon 38 extending through the whole distance between the left and right subclavian 23L, 23R, or left subclavian 23L and innominate arteries 41. Inflation of this balloon 38 during cardiac systole whether inserted via the left or right arm will not only occlude the orifices of the right subclavian 23R, right carotid 26R and left subclavian 23L arteries, but also will cover the orifice 92 of the left common carotid artery 26L, thus completely preventing the emboli 28 from entering cerebral circulation via all potential ways.

It is to be understood that although described herein as inflated or deflated, the occluding balloon 38 may always have some degree of inflation. As such, during systole the occluding balloon 38 may be said to have a greater degree of inflation than when in the diastole phase. Therefore, the occluding balloon 38 can be inflated during the diastole phase, but to a lesser degree such that lessor occlusion occurs than when in the systole phase.

Figure 23:
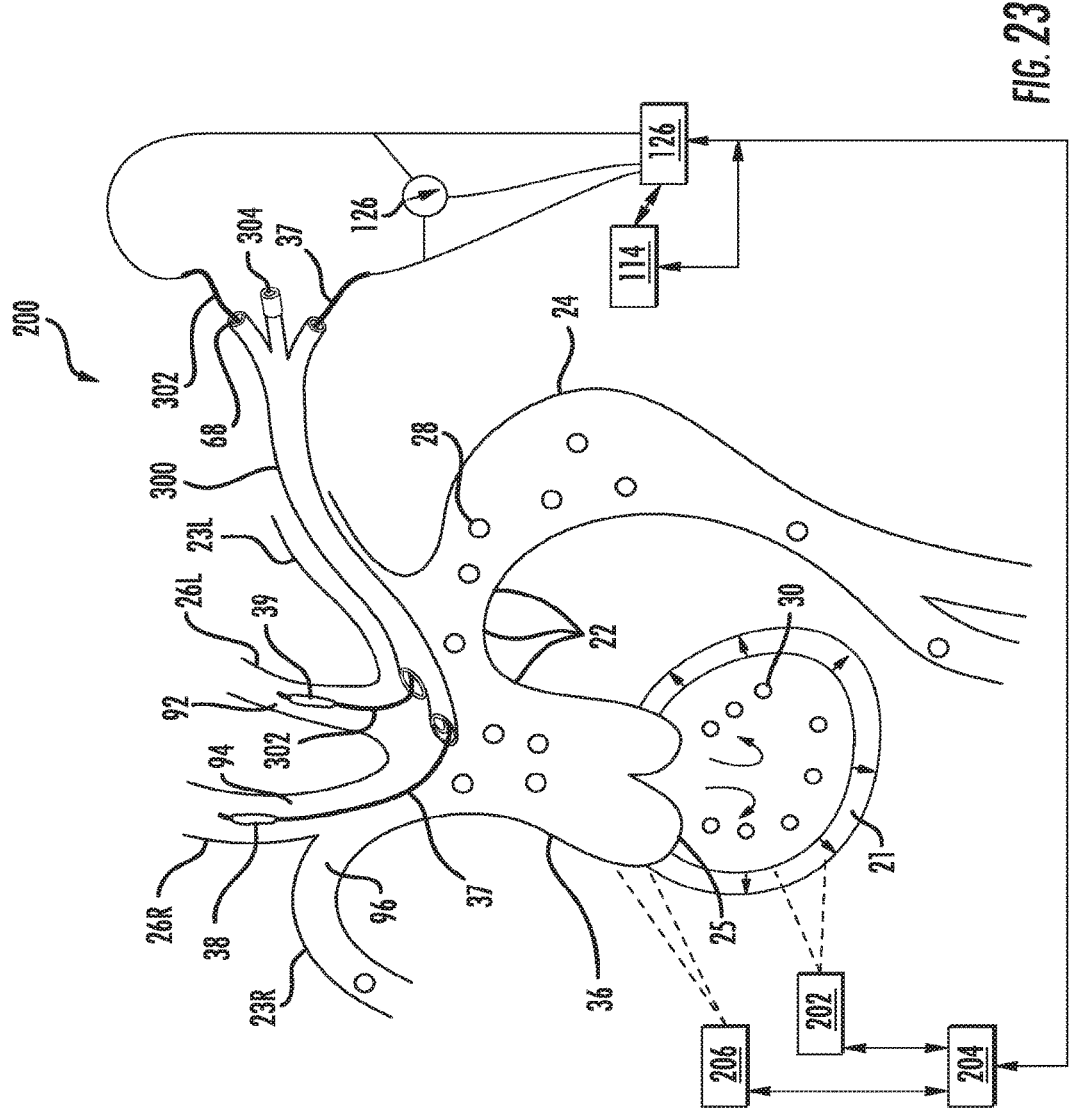
FIG. 23 is a front view of an alternate exemplary embodiment of the system with two catheters with the heart in a diastole phase.
Figure 24:
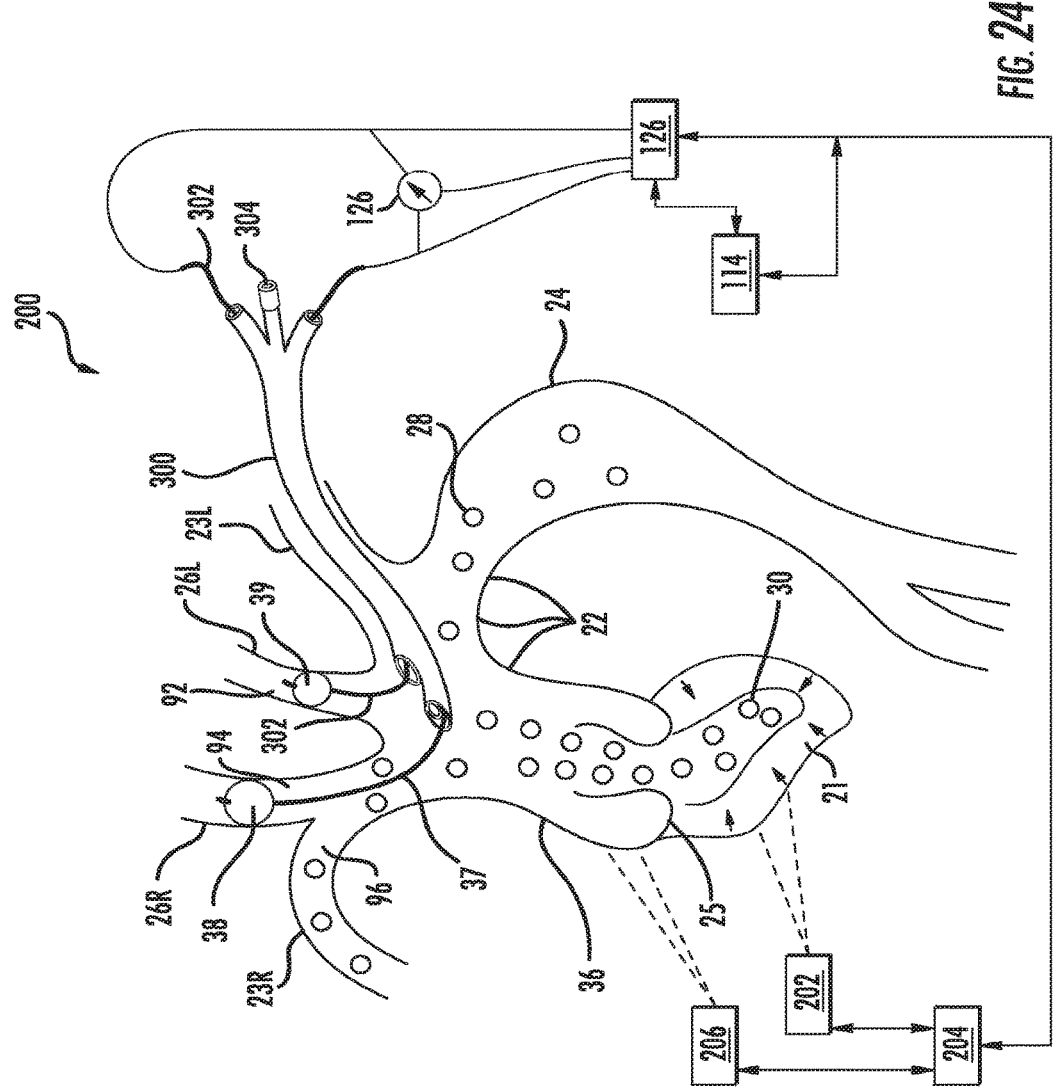
FIG. 24 is a front view of the system of FIG. 23 with the heart in a systole phase.

FIGS. 23 and 24 illustrate another embodiment of the system 200 in which the occluding catheter 37 is used for dynamic occlusion. A second occluding catheter 302 is present and is used along with the first occluding catheter 37 in the system 200. An introduction sheath 300 can be employed in order to properly position the occluding catheters 37, 302 in the circulatory system. The introduction sheath 300 is placed through the left subclavian 23L artery and its distal end is located in the aortic arch 22. The occluding catheters 37, 302 are advanced through the introduction sheath 300 and extend out of the distal end. The first occluding catheter 37 is moved into the right carotid artery 26R, and the second occluding catheter 302 is moved into the left carotid artery 26L.

With reference to FIG. 23, the first occluding catheter 37 has an occluding balloon 38 that is within the right carotid artery 26R, and the second occluding catheter 302 has an occluding balloon 39 that is located within the left carotid artery 26L. The occluding balloons 38 and 39 are both deflated and the heart 21 is in the diastole phase to allow some blood flow to go into the carotid arteries 26R, 26L. The system 200 may monitor the heart cycle and cause deflation of the balloons 38 and 39 at the appropriate phase. The introduction sheath 300 has a measurement port 304 through which a pressure measurement can be made, or an instrument can be introduced. The introduction sheath 300 need not be used in other arrangements as instead the balloons 38 and 39 can be otherwise moved into position within the carotid arteries 26R, 26L.

In FIG. 24, the heart 21 has entered the systole phase and emboli 28 is injected therefrom. The system 200 causes the actuation device 126 to inflate the balloons 38 and 39 to block the right and left carotid arteries 26R, 26L. The emboli 28 is diverted into the right subclavian artery 23R and into the descending aorta 24. The emboli 28 is prevented from flowing past the inflated balloons 38, 39 but could flow into the left subclavian artery 23L. The introduction sheath 300 may be removed in some instances once the occluding catheters 37, 302 are properly positioned.

The system 200 may employ any number of occluding catheters 37 and occluding balloons 38. They can be positioned anywhere in the aortic arch 22, or arteries 23R, 23L, 26R or 26L. The system 200 may employ any type of structure capable of dynamically blocking flow through the carotid arteries 26L and/or 26R based on the cycle of the heart 21.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A method for the prevention of stroke during a surgical procedure, comprising:
applying occlusion of blood flow to a carotid artery of a patient when the patient is undergoing a surgical procedure, wherein the occlusion is applied from a location inside of the patient, wherein the occlusion at least partially blocks blood flow to the carotid artery and at the same time permits blood flow through an aorta and into distal vasculature;
removing the occlusion to allow more blood flow through the carotid artery than when the occlusion was applied; and
repeating the steps of applying and removing the occlusion a plurality of times during the surgical procedure in a cyclical nature based upon whether the heart is in the systole phase or in the diastole phase.

2. The method as set forth in claim 1, further comprising the step of initially applying occlusion to the carotid artery of the patient for an initial period of time without regard to the phases of the heart, wherein after the step of initially applying occlusion the method moves to the applying occlusion, removing, and repeating steps.

3. The method as set forth in claim 1, comprising inserting of a balloon catheter into the patient at an area selected from the group consisting of: an innominate artery, a right carotid artery, a left carotid artery, a subclavian artery and an aortic arch, wherein an occluding balloon of the balloon catheter is inflated to occlude blood flow to at least one of the right carotid artery and the left carotid artery;
wherein the inflating the occluding balloon is initiated by an actuation device; and
wherein the inflation is applied in a cyclical nature based upon a cardiac cycle that causes the resulting steps of the applying and removing cyclical occlusion.

4. The method as set forth in claim 3, wherein the occluding balloon is inflated to such a degree that blood flow to at least one of the right carotid artery and the left carotid artery is completely blocked.

5. A method for the prevention of stroke during a surgical procedure, comprising:
applying occlusion of blood flow to a carotid artery of a patient when the patient is undergoing a surgical procedure, wherein the occlusion is applied from a location inside of the patient, wherein the occlusion at least partially blocks blood flow to the carotid artery;
removing the occlusion to allow more blood flow through the carotid artery than when the occlusion was applied; and
repeating the steps of applying and removing the occlusion a plurality of times during the surgical procedure in a cyclical nature based upon whether the heart is in the systole phase or in the diastole phase;
inserting of a balloon catheter into the patient at an area selected from the group consisting of: an innominate artery, a right carotid artery, a left carotid artery, a subclavian artery and an aortic arch, wherein an occluding balloon of the balloon catheter is inflated to occlude blood flow to at least one of the right carotid artery and the left carotid artery;
wherein the inflating the occluding balloon is initiated by an actuation device;
wherein the inflation is applied in a cyclical nature based upon a cardiac cycle that causes the resulting steps of the applying and removing cyclical occlusion;
wherein the inflation to cause the occlusion of the carotid artery is applied during a systole phase of the cardiac cycle, wherein a lesser degree of the inflation is applied to the occluding balloon during the diastole phase of the cardiac cycle than is applied during the systole phase of the cardiac cycle.

6. The method as set forth in claim 5, wherein the lesser degree of inflation applied to the occluding balloon during the diastole phase is no inflation such that the occluding balloon is fully deflated during the diastole phase.

7. A method for the prevention of stroke during a surgical procedure, comprising:
applying occlusion of blood flow to a carotid artery of a patient when the patient is undergoing a surgical procedure, wherein the occlusion is applied from a location inside of the patient, wherein the occlusion at least partially blocks blood flow to the carotid artery;
removing the occlusion to allow more blood flow through the carotid artery than when the occlusion was applied; and
repeating the steps of applying and removing the occlusion a plurality of times during the surgical procedure in a cyclical nature based upon whether the heart is in the systole phase or in the diastole phase;
inserting of a balloon catheter into the patient at an area selected from the group consisting of: an innominate artery, a right carotid artery, a left carotid artery, a subclavian artery and an aortic arch, wherein an occluding balloon of the balloon catheter is inflated to occlude blood flow to at least one of the right carotid artery and the left carotid artery;
wherein the inflating the occluding balloon is initiated by an actuation device;
wherein the inflation is applied in a cyclical nature based upon a cardiac cycle that causes the resulting steps of the applying and removing cyclical occlusion;
wherein the systole phase has an early portion, and wherein a lesser degree of inflation is applied to the occluding balloon during the early portion of the systole phase than to a remaining portion of the systole phase.

8. A method for the prevention of stroke during a surgical procedure, comprising:
applying occlusion of blood flow to a carotid artery of a patient when the patient is undergoing a surgical procedure, wherein the occlusion is applied from a location inside of the patient, wherein the occlusion at least partially blocks blood flow to the carotid artery;
removing the occlusion to allow more blood flow through the carotid artery than when the occlusion was applied; and
repeating the steps of applying and removing the occlusion a plurality of times during the surgical procedure in a cyclical nature based upon whether the heart is in the systole phase or in the diastole phase;
inserting of a balloon catheter into the patient at an area selected from the group consisting of: an innominate artery, a right carotid artery, a left carotid artery, a subclavian artery and an aortic arch, wherein an occluding balloon of the balloon catheter is inflated to occlude blood flow to at least one of the right carotid artery and the left carotid artery;
wherein the inflating the occluding balloon is initiated by an actuation device;
wherein the inflation is applied in a cyclical nature based upon a cardiac cycle that causes the resulting steps of the applying and removing cyclical occlusion;
wherein the inflation of the occluding balloon to occlude blood flow to at least one of the right carotid artery and the left carotid artery is synchronized by using a cardiac monitoring device that monitors the heart;

wherein the cardiac cycle is the cardiac cycle of the heart;

wherein the cardiac monitoring device obtains data on when the cardiac cycle is in the systole phase and when the cardiac cycle is in the diastole phase; and further comprising obtaining data from the cardiac monitoring device by a synchronization device, wherein the synchronization device causes the actuation device to cause inflation of the occluding balloon based upon the data obtained from the cardiac monitoring device such that the occlusion is applied during a majority of the systole phase and is not applied during a majority of the diastole phase.

9. The method as set forth in claim 8, wherein the cardiac monitoring device is selected from the group consisting of an electrocardiogram, a device for monitoring blood pressure waveform, a device for measuring cardiac pacing activity, and a pulse oximetry device.

10. A method for the prevention of stroke during a surgical procedure, comprising:

applying occlusion of blood flow to a carotid artery of a patient when the patient is undergoing a surgical procedure, wherein the occlusion is applied from a location inside of the patient, wherein the occlusion at least partially blocks blood flow to the carotid artery;

removing the occlusion to allow more blood flow through the carotid artery than when the occlusion was applied; and repeating the steps of applying and removing the occlusion a plurality of times during the surgical procedure in a cyclical nature based upon whether the heart is in the systole phase or in the diastole phase;

inserting of a balloon catheter into the patient at an area selected from the group consisting of: an innominate artery, a right carotid artery, a left carotid artery, a subclavian artery and an aortic arch, wherein an occluding balloon of the balloon catheter is inflated to occlude blood flow to at least one of the right carotid artery and the left carotid artery;

wherein the inflating the occluding balloon is initiated by an actuation device;

wherein the inflation is applied in a cyclical nature based upon a cardiac cycle that causes the resulting steps of the applying and removing cyclical occlusion;

wherein the actuation device is a pressure source that delivers a fluid to the occluding balloon, wherein the occluding balloon is a distal occluding balloon that is located in the left carotid artery and occludes the left carotid artery when inflated;

wherein the balloon catheter has a shaft that has a proximal occluding balloon that is spaced from the distal occluding balloon by a segment of the shaft, wherein the proximal occluding balloon is located in the innominate artery and is inflated by the actuation device to occlude blood flow to the right carotid artery and a right subclavian artery, wherein the inflation of the proximal occluding balloon is applied in a cyclical nature based upon the cardiac cycle, wherein the cyclical inflation of the proximal occluding balloon in turn causes a resulting cyclical occlusion.

11. The method as set forth in claim 10, wherein the shaft is a first shaft, and wherein the occluding balloon is a first occluding balloon, and wherein the first shaft and the first occluding balloon are part of the occluding catheter that is a first occluding catheter, wherein when the first occluding balloon is inflated blood flow to one of but not both of the right and left carotid arteries is occluded, and further comprising:

providing a second occluding catheter that has a second shaft that carries a second occluding balloon, wherein the second occluding balloon is inflated to occlude blood flow to the other one of the right or left carotid arteries that is not occluded by the first occluding balloon, wherein the actuation device causes inflation of the second occluding balloon, wherein the inflation of the second occluding balloon is applied in a cyclical nature based upon the cardiac cycle, wherein the cyclical inflation of the second occluding balloon in turn causes a resulting cyclical occlusion.

12. The method as set forth in claim 11, wherein the actuation device causes inflation of the first occluding balloon and the second occluding balloon simultaneously.

13. A method for the prevention of stroke during a surgical procedure, comprising:

applying occlusion of blood flow to a carotid artery of a patient when the patient is undergoing a surgical procedure, wherein the occlusion is applied from a location inside of the patient, wherein the occlusion at least partially blocks blood flow to a carotid artery, wherein the occlusion is initiated automatically when the emboli are detected in a circulatory system of the patient;

removing the occlusion to allow more blood flow to the carotid artery than when the occlusion was applied when the emboli are not detected in the circulatory system of the patient; and repeating the steps of applying and removing the occlusion a plurality of times during the surgical procedure based upon whether the emboli are detected or are not detected in the circulatory system of the patient.

14. The method as set forth in claim 13, wherein the process of detection of emboli in the circulatory system of the patient is achieved by using a method selected from the group consisting of echocardiography, arterial Doppler ultrasound, and cerebral oximetry;

wherein the occlusion of the blood flow is activated when the presence of emboli in the circulatory system is detected.

* * * * *